United States Patent [19]

Tarcha et al.

[11] Patent Number: 5,376,556
[45] Date of Patent: Dec. 27, 1994

[54] SURFACE-ENHANCED RAMAN SPECTROSCOPY IMMUNOASSAY

[75] Inventors: Peter J. Tarcha, Lake Villa; Thomas E. Rohr, Gurnee; James J. Markese, Downers Grove, all of Ill.; Therese Cotton, Ames, Iowa; Bernard N. Rospendowski, Glasgow, United Kingdom

[73] Assignee: Abbott Laboratories, Abbott Park, Ill.

[21] Appl. No.: 944,138

[22] Filed: Sep. 11, 1992

Related U.S. Application Data

[63] Continuation-in-part of Ser. No. 790,106, Nov. 7, 1991, Pat. No. 5,266,498, which is a continuation of Ser. No. 428,230, Oct. 27, 1989, abandoned.

[51] Int. Cl.$^5$ .......................................... G01N 33/553
[52] U.S. Cl. ................... 436/525; 435/968; 436/164; 436/514; 436/524; 436/536; 436/538; 436/541; 436/805
[58] Field of Search ............... 435/7.92, 7.93, 7.94, 435/968, 973, 975; 436/164, 524, 525, 536, 538, 541, 805, 808, 824, 514

[56] References Cited

U.S. PATENT DOCUMENTS

| 4,094,647 | 6/1978 | Deutsch et al. | 436/810 |
| 4,134,792 | 1/1979 | Boguslaski et al. | 436/815 |
| 4,186,146 | 1/1980 | Butte, Jr. et al. | 260/570.9 |
| 4,235,601 | 11/1980 | Deutsch et al. | 422/56 |
| 4,298,688 | 11/1981 | Kallies | 422/56 |
| 4,361,537 | 11/1982 | Deutsch et al. | 422/56 |

(List continued on next page.)

FOREIGN PATENT DOCUMENTS

0088636A2 9/1983 European Pat. Off.
0259157A1 3/1988 European Pat. Off.
0267006A2 5/1988 European Pat. Off.

OTHER PUBLICATIONS

Rohr et al, "Immunoassay Employing Surface Enhanced Raman Spectroscopy", *Analytical Biochemistry*, 1989, 182, pp. 388–398.

Hildebrandt et al, "Enhanced Resonance Raman Spectroscopy of Rhodamine 6G Absorbed on Colloidal Silver", *J. Physical Chemistry*, 1984, 88, 5935–5944.

C. H. Keller et al., "The Abbott IMx ® and IMx SELECT ™ Systems", J. Clinical Immunoassay, v.14, No. 2, 1991.

M. Fiore et al., "The Abbott IMx ™ Automated Benchtop Immunochemistry Analyzer System", Clinical Chemistry, V.34, No. 9, 1988.

P. C. Hiemenz, "*Principles of Colloid and Surface Chemistry*", 1977, pp. 352–491.

(List continued on next page.)

*Primary Examiner*—David Saunders
*Assistant Examiner*—Christopher L. Chin
*Attorney, Agent, or Firm*—Richard D. Schmidt

[57] ABSTRACT

A method, composition, device, apparatus, and kit for the determination of the presence or amount of an analyte by monitoring an analyte-mediated ligand binding event in a test mixture which contains the analyte to be assayed, a specific binding member, a Raman-active label, and a particulate having a surface capable of inducing a surface-enhanced Raman light scattering. The test mixture is illuminated with a radiation sufficient to cause the Raman-active label in the test mixture to emit a detectable Raman spectrum. The differences in the detected surface-enhanced Raman scattering spectra are dependent upon the amount of the analyte present in the test mixture. Thus, by monitoring these differences, the presence or amount of the analyte are determined.

6 Claims, 10 Drawing Sheets

U.S. PATENT DOCUMENTS

| | | | |
|---|---|---|---|
| 4,366,241 | 12/1982 | Tom et al. | 422/56 |
| 4,517,288 | 5/1985 | Giegel et al. | 422/56 |
| 4,740,468 | 4/1988 | Weng et al. | 436/514 |
| 4,948,726 | 8/1990 | Longoria | 435/7.93 |
| 5,102,788 | 4/1992 | Cole | 436/523 |
| 5,266,498 | 11/1993 | Tarcha et al. | 436/525 |

OTHER PUBLICATIONS

D. H. Napper, "Steric Stabilization", J. of Colloid and Interface Science, v. 58, No. 2, 1977.

R. I. Feigen and D. H. Napper, "Depletion Stabilization and Depletion Flocculation", J. Of Colloid and Interface Science, v. 75, No. 2, (1980).

P. K. Aravind, A. Nitzan, and H. Meitu, "The Interaction Between Electromagnetic Resonances And Its Role In Spectroscopic Studies Of Molecules Adsorbed On Colloidal Particles Or Metal Spheres", Surface Science, 110 (1981).

H. Metiu, "Surface Enhanced Spectroscopy", Progress in Surface Science, v. 17 (1984).

R. F. Zuk et al., "Enzyme Immunochromatography–A Quantitative Immunoassay Requiring No Instrumentation", Clinical Chemistry, v.31, No. 7, (1985).

F. Ni et al., "Surface–Enhanced Resonance Raman Study of Avidin–Dye Interactions: A Model for Chromophore–Containing Proteins", J. of Raman Spectroscopy, v. 19, pp. 429–438, 1988.

P. C. Lee et al., "Adsorption and Surface–Enhanced Raman of Dyes on Silver and Gold Sols[1]", J. Physical Chemistry, v. 86, No. 17, pp. 3391–3395, 1982.

FIG. 8
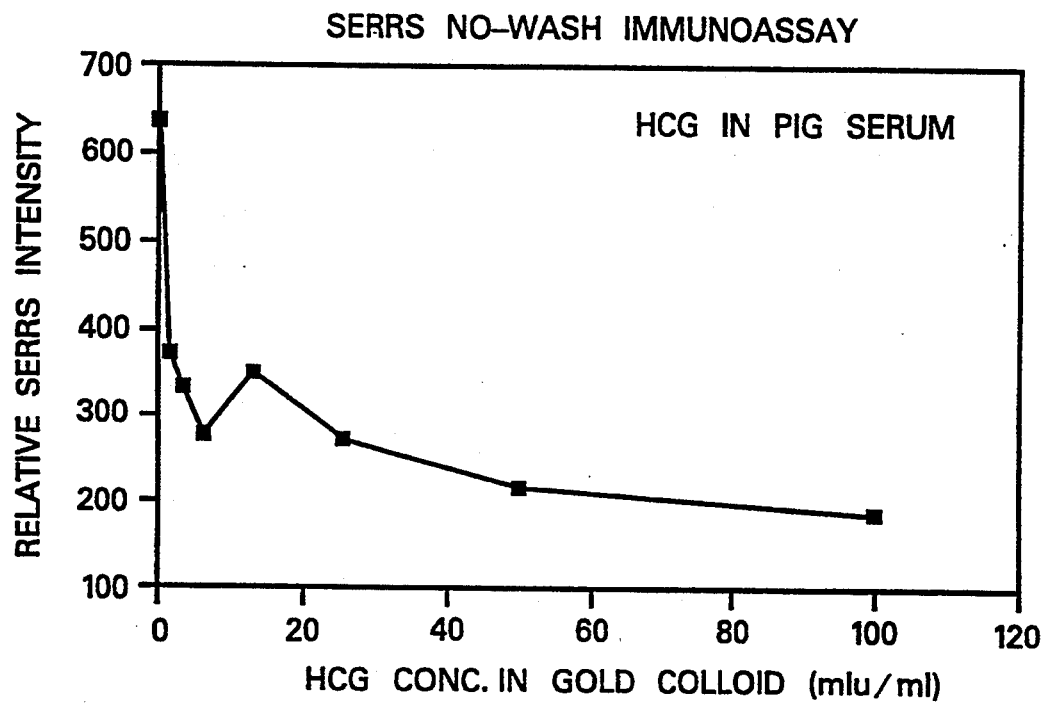
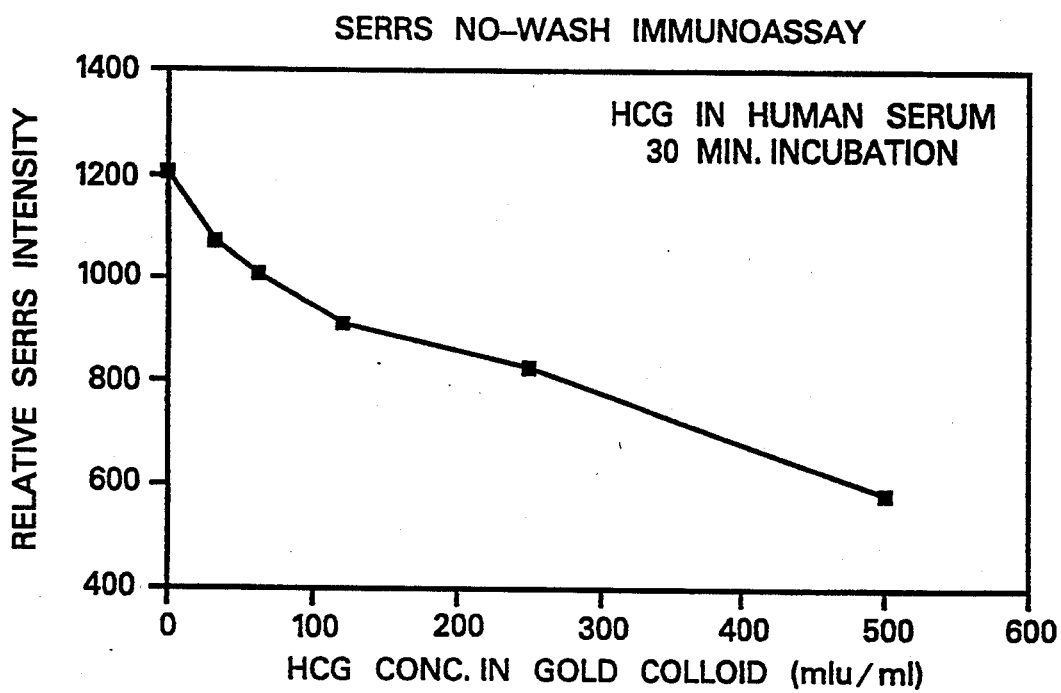
FIG. 9

FIG. 10
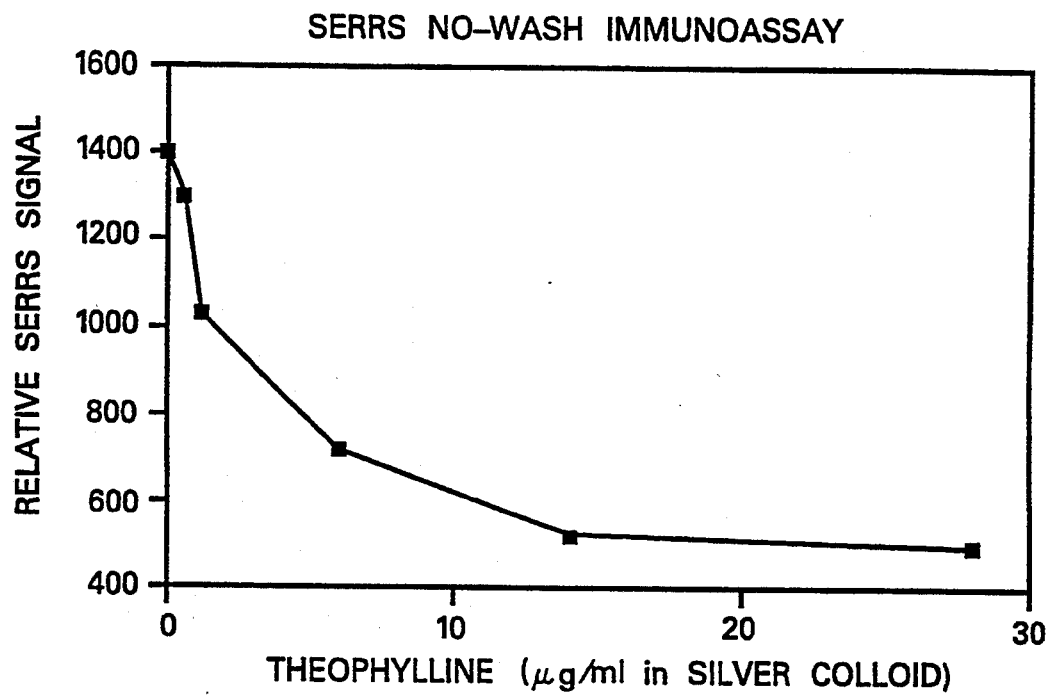
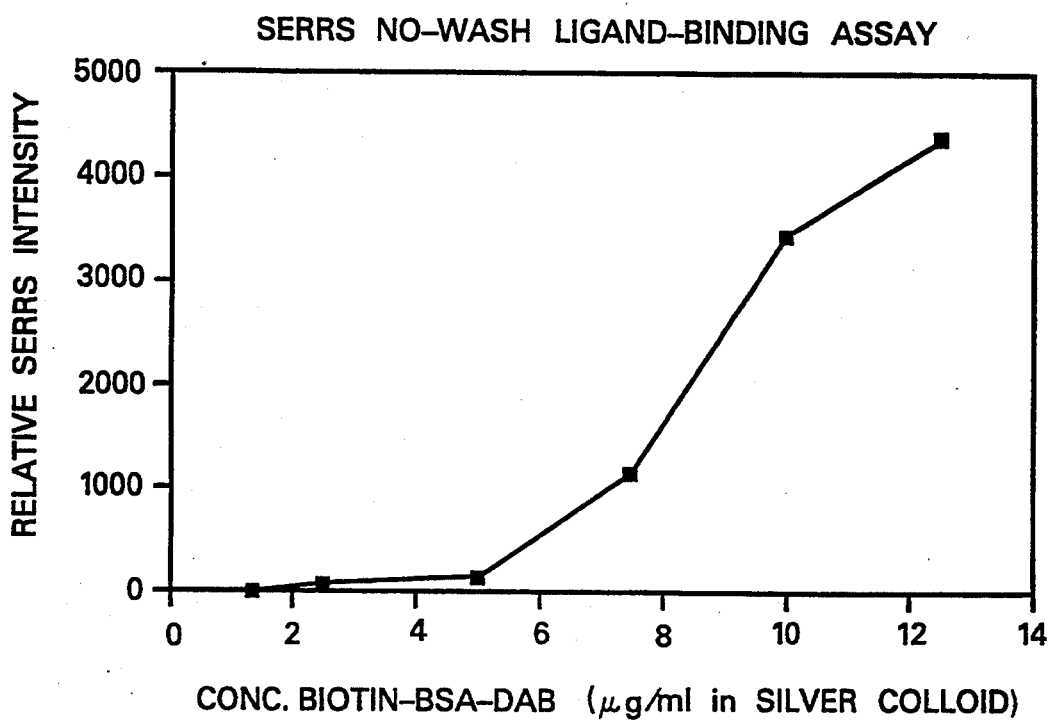
FIG. 11

SURFACE-ENHANCED RAMAN SPECTROSCOPY IMMUNOASSAY

This application is a continuation-in-part of U.S. patent application Ser. No. 07/790,106, filed Nov. 7, 1991 now U.S. Pat. No. 5,266,498, which is a continuation of U.S. patent application Ser. No. 07/428,230, filed Oct. 27, 1989, now abandoned.

BACKGROUND OF THE INVENTION

A. Field of the Invention

This invention relates to a novel method, composition, and kit for the determination of the presence or amount of an analyte in a test sample by monitoring an analyte-mediated ligand binding event in a test mixture. In particular, this invention relates to a novel method, composition, and kit for the determination of the presence or amount of an analyte in a test sample by monitoring differences and changes in the surface-enhanced Raman scattering spectrum in a test mixture which comprises the test sample, a specific binding member, a Raman-active label, and a particulate having a surface capable of inducing surface-enhanced Raman light scattering.

The affinity of binding displayed by certain molecules (referred to here as binding molecules) towards other specific molecules (referred to here as ligands) is used commonly as the basis of assays to measure the quantity of a particular binding molecule or ligand in a sample.

The two molecules involved in forming a binding molecule-ligand complex are also referred to as a specific binding pair. One member of a specific binding pair is referred to as a specific binding member. This invention includes methods for performing assays using specific binding pairs of binding molecules and ligands, with surface-enhanced Raman light scattering as the method of detection. This invention also includes materials and kits used in performing the assays.

An assay is a test (1) to detect the presence of a substance in a sample, (2) to identify a substance in a sample, and/or (3) to measure the amount of a substance in a sample. In the terminology of this art, the substance that the assay is designed to detect, identify, or measure is called an "analyte."

Ligand binding assays are especially relevant to medical diagnostics. In modern medical practice, ligand binding assays are routinely run on patients' blood, urine, saliva, etc. in order to determine the presence or levels of antibodies, antigens, hormones, medications, poisons, toxins, illegal drugs, and others.

New, better, less expensive, and faster assays can advance the level of health care. Such assays can provide a physician with more and better information about a patient and do so consistent with reasonable cost. In addition, by making assays easier and less expensive, a higher level of health care can be extended to less developed parts of the world. Ligand binding assays are also being used to monitor groundwater contamination, toxins and pesticides in foods, industrial biological processes, and in many areas of biological research.

B. Present Ligand Binding Assays

For many assays it is required that minute quantities of a certain substance (the analyte) be detected and measured in the presence of much larger quantities of other substances. This is possible because the high affinity a binding molecule can have for a ligand can result in a high degree of specificity of binding for that particular ligand, irrespective of the presence of other substances. The most common ligand binding assays are immunoassays.

In an immunoassay, an antibody serves as a binding molecule which specifically binds an antigen, which serves as the ligand, thereby forming a specific binding pair. In order to measure the extent of the antibody/antigen binding, one member of the specific binding pair is tagged or labeled with a traceable substance. The unique properties of the traceable substance allow its presence, and hence the presence of the specific binding member to which it is attached, to be detected or measured. The labeled member of the specific binding pair is referred to as the indicator reagent.

In a direct immunoassay, the quantity of indicator reagent bound to the other member of the specific binding pair is measured. In an indirect immunoassay, the degree of inhibition of binding of the indicator reagent to the other member of the specific binding pair by the analyte is measured.

The individual members of a specific binding pair do not have to be antigens or antibodies, however. Any two molecules having affinity for each other may comprise a specific binding pair and may form the basis of a ligand-binding assay. Other examples of such specific binding pairs are: lectins and the complex carbohydrates to which they bind, hormones and their receptors, any effector molecule and its receptor, binding molecules designed through molecular modeling and synthesized specifically to bind another molecule, and other molecules with mutual affinity such as avidin and biotin.

Two commonly-used immunoassay techniques are radioimmunoassay (RIA) and enzyme immunoassay (EIA), both of which employ a labeled specific binding member as an indicator reagent. RIA uses a radioactive isotope as the traceable substance attached to a specific binding member. Because the radioactive isotope can be detected in very small amounts, it can be used to detect or quantitate small amounts of analyte. There are, however, a number of substantial drawbacks associated with RIA. These drawbacks include the special facilities and extreme caution that are required in handling radioactive materials, the high costs of such reagents and their unique disposal requirements.

EIA uses an enzyme as the label attached to a specific binding member which in the presence of its substrate produces a detectable substance or signal. This enzyme-labeled specific binding member then serves as the indicator reagent, and enzymatic activity is used to detect its binding. While EIA does not have some of the same disadvantages as RIA, EIA techniques require the addition of substrate materials to elicit the detectable enzyme reaction. Another disadvantage is that enzyme stability and rate of substrate turnover are temperature sensitive, the former decreasing and the latter increasing with temperature.

A drawback common to all of these assay configurations is the necessity of separating unbound labeled reagent from that bound to the analyte. This usually entails wash steps which are tedious when the assays are performed manually and require complicated robotics in automated formats.

Immunoassays may also be performed by automated instruments. Examples of such instruments are the TDx®, IMx®, and IMx SELECT™ analyzers which are commercially available from Abbott Laboratories, Abbott Park, Ill. These instruments are used to measure analyte concentrations in biological fluids such as serum, plasma and whole blood. The IMx ® and IMx SELECT ™ analyzers have been described by Charles H. Keller, et al., "The Abbott IMx ® and IMx SELECT ™ System," J. Clin. Immunoassay, 14, 115, 1991; and M. Fiore et al., "The Abbott IMx ™ Automated Benchtop Immunochemistry Analyzer System," Clin. Chem., 34, 1726, 1988.

Other types of assays use the so-called "dipstick" and "flowthrough" methods. With these methods, a test sample is applied to the "dipstick" or "flowthrough" device, and the presence of the analyte is indicated by a visually detectable signal generated by a color forming reaction. Flowthrough devices generally use a porous material with a reagent immobilized at a capture situs on a matrix layered thereon or incorporated therein. The test sample is applied to the device and flows through the porous material. The analyte in the sample then reacts with the reagent(s) to produce a detectable signal on the porous material. Such devices have proven useful for the qualitative determination of the presence of an analyte.

More recently, assay techniques using metallic colloid particles have been developed. The specific binding member to be labeled is coated onto the metal or colloid, particles by adsorption and the metal particles become the label. Localization of these labeled binding members on a solid support via an immunoreaction can produce a signal that is visually detectable, as well as measurable by an instrument.

Fluorescent and visible dyes and spin labels have also been used as labels in ligand binding assays.

All of these binding molecule-ligand assays have inherent drawbacks. The use of Raman light scattering as a means of detecting or measuring the presence of a labeled specific binding member, avoids some of these drawbacks, as explained below.

C. Rayleigh Light Scattering

For many years, it has been known that when certain molecules are illuminated by a beam of light, for example ultraviolet, visible, or near infrared, a small fraction of the incident photons are retained momentarily by some of the molecules, causing a transition of the energy levels of some of those molecules to higher vibrational levels of the ground electronic state. These higher vibrational levels are called virtual states. Most of the time, these are elastic collisions, and the molecules return to their original vibrational level by releasing photons. Photons are emitted in all directions at the same wavelength as the incident beam (i.e., they are scattered). This is called Rayleigh scattering.

D. Raman Light Scattering

In 1928, C. V. Raman discovered that when certain molecules are illuminated, a small percentage of the molecules which have retained a photon do not return to their original vibrational level after remitting the retained photon, but drop to a different vibrational level of the ground electronic state. The radiation emitted from these molecules will therefore be at a different energy and hence a different wavelength. This is referred to as Raman scattering.

If the molecule drops to a higher vibrational level of the ground electronic state, the photon emitted is at a lower energy or longer wavelength than that absorbed. This is referred to as Stokes-shifted Raman scattering. If a molecule is already at a higher vibrational state before it absorbs a photon, it can impart this extra energy to the remitted photon thereby returning to the ground state. In this case, the radiation emitted is of higher energy (and shorter wavelength) and is called anti-Stokes-shifted Raman scattering. In any set of molecules under normal conditions, the number of molecules at ground state is always much greater than those at an excited state, so the odds of an incident photon interacting with an excited molecule and being scattered with more energy than it carried upon collision is very small. Therefore, photon scattering at frequencies higher than that of the incident photons (anti-Stokes frequencies) is minor relative to that at frequencies lower than that of the incident photons (Stokes frequencies). Consequently, it is the Stokes frequencies that are usually analyzed.

The amount of energy lost to, or gained from, a molecule in this way is quantized, resulting in the scattered photons having discrete wavelength shifts. These wavelength shifts can be measured by a spectrometer. Raman scattering was considered to have the potential to be useful as an analytical tool to identify certain molecules, and as a means of studying molecular structure. However, other methods, such as infrared spectroscopy, proved to be more useful.

E. Resonance Raman Scattering

Interest in Raman spectroscopy was renewed with the advent of the laser as a light source. Its intense coherent light overcame some of the sensitivity drawbacks of Raman spectroscopy. Moreover, it was discovered that when the wavelength of the incident light is at or near the maximum absorption frequency of the molecule, and hence can cause electronic as we! 1 as vibrational transitions in the molecules, resonance Raman scattering is observed. With resonance Raman scattering, the re-emitted photons still show the differences in vibrational energy associated with Raman scattering. However, with resonance Raman scattering, the electronic vibrational absorption is approximately 1000 times more efficient. Even with the increased signal from resonance Raman scattering, its usefulness as an analytic tool was limited due to its still comparatively weak signal. The relatively recent discovery of the surface enhancement effect, however, has provided a means to further dramatically enhance Raman scattering intensity.

F. Surface Enhanced Raman Scattering

A significant increase in the intensity of Raman light scattering can be observed when molecules are brought into close proximity to (but not necessarily in contact with) certain metal surfaces. The metal surfaces need to be "roughened" or coated with minute metal particles. Metal colloids also show this signal enhancement effect. The increase in intensity can be on the order of several million-fold or more. In 1974, Dr. Richard P. Van Duyne was the first to recognize this effect as a unique phenomenon and coined the term "surface enhanced Raman scattering" (SERS).

The cause of the SERS effect is not completely understood; however, current thinking envisions at least two separate factors contributing to SERS. First, the metal surface contains minute irregularities. These irregularities can be thought of as spheres (in a colloid, they are spheroidal or nearly so). Those particles with diameters of approximately 1/10th the wavelength of the incident light are considered to contribute most to the effect. The incident photons induce a field across the particles which, being metal, have very mobile electrons.

In certain configurations of metal surfaces or particles, groups of surface electrons can be made to oscillate in a collective fashion in response to an applied oscillating electromagnetic field. Such a group of collectively oscillating electrons is called a "plasmon." The incident photons supply this oscillating electromagnetic field. The induction of an oscillating dipole moment in a molecule by incident light is the source of the Raman scattering. The effect of the resonant oscillation of the surface plasmons is to cause a large increase in the electromagnetic field strength in the vicinity of the metal surface. This results in an enhancement of the oscillating dipole induced in the scattering molecule and hence increases the intensity of the Raman scattered light. The effect is to increase the apparent intensity of the incident light in the vicinity of the particles.

A second factor considered to contribute to the SERS effect is molecular imaging. A molecule with a dipole moment, which is in close proximity to a metallic surface, will induce an image of itself on that surface of opposite polarity (i.e., a "shadow" dipole on the plasmon). The proximity of that image is thought to enhance the power of the molecules to scatter light. Put another way, this coupling of a molecule having an induced or distorted dipole moment to the surface plasmons greatly enhances the excitation probability. The result is a very large increase in the efficiency of Raman light scattered by the surface-absorbed molecules.

The SERS effect can be enhanced through combination with the resonance Raman effect. The surface-enhanced Raman scattering effect is even more intense if the frequency of the excitation light is in resonance with a major absorption band of the molecule being illuminated. The resultant Surface Enhanced Resonance Raman Scattering (SERRS) effect can result in an enhancement in the intensity of the Raman scattering signal of seven orders of magnitude or more.

G. Application of SERS to Immunoassays

The SERS effect has been used by physical and analytical chemists to follow chemical reactions on electrode surfaces in order to study molecular surface structure and dynamics. Recently, the technique has also been applied to biological molecules containing Raman-active prosthetic groups, such as hemes.

Up until now, there has been no application of the SERS effect to immunodiagnostics.

Utilization of this technology in immunodiagnostics offers several unique advantages. Because of the extraordinary dependence of the SERS signal upon close association with a suitable surface, only those reporter molecules which have become immobilized on or near the SERS-active surface will contribute a significant signal, while the signal contribution of those remaining in solution will be negligible. Molecules bound in different environments or different orientations can exhibit differences in their Raman scattering characteristics.

SUMMARY OF THE INVENTION

According to one feature of the present invention there is provided a method for assaying, or determining the presence or amount of an analyte by: Monitoring an analyte-mediated ligand binding event in a test mixture containing the test sample, specific binding member, Raman-active label and a particulate by allowing a complex to be formed, in the test mixture, between an analyte, a specific binding member, a Raman-active label, and a particulate wherein the particulate is characterized by having a surface capable of inducing a surface-enhanced Raman light scattering; illuminating the test mixture with a radiation sufficient to cause the Raman-active label in the complex to emit a detectable Raman spectrum; and monitoring differences in the detected surface-enhanced Raman scattering spectra, the differences being dependent upon the amount of the analyte present in the test mixture.

According to another feature of the present invention, there is provided a method for assaying, or determining the presence or amount of an analyte in a test sample by: Monitoring an analyte-mediated ligand binding event in a test mixture by forming a test mixture comprising the test sample, a labeled analyte-analog and a particulate capture reagent comprising the specific binding member immobilized on a particulate having a surface capable of inducing surface-enhanced Raman light scattering wherein the labeled analyte-analog comprises an analyte-analog molecule expressing an analyte epitope recognized by a specific binding member, said analyte-analog being attached to a Raman-active label either directly, or indirectly, through an intervening molecule, then, allowing the labeled analyte-analog to be bound to the specific binding member on the particulate, wherein the extent of the binding of the labeled analyte-analog to the specific binding member on the particulate is affected by the presence of the analyte; then, illuminating the test mixture with a radiation sufficient to cause the Raman-active label on the bound labeled analyte-analog in the test mixture to emit a detectable Raman spectrum; and then monitoring difference in the detected surface-enhanced Raman scattering spectra, the differences being dependent upon the amount of the analyte present in the test mixture.

According to another feature of the present invention, there is provided a method for assaying, or determining the presence or amount of, an analyte in a test sample by monitoring an analyte-mediated ligand binding event in a test mixture by: Forming the test mixture from the test sample containing the analyte and a particulate capture reagent comprising a specific binding member conjugated to a particulate having a surface capable of inducing a surface-enhanced Raman light scattering and also having associated with it a Raman-active label: then applying the test mixture onto a chromatographic material having a proximal end and a distal end, wherein the chromatographic material comprises a capture reagent immobilized in a capture situs and capable of binding to the analyte; then allowing the test mixture to travel from the proximal end toward the distal end by capillary action; then illuminating the capture situs with a radiation sufficient to cause a detectable Raman spectrum; and, then monitoring differences in the detected surface-enhanced Raman scattering spectra, the differences being dependent upon the amount of the analyte present in the test mixture.

According to yet another feature of the present invention, there is provided a composition to be used for determining the presence or amount of an analyte in a test sample by monitoring an analyte-mediated ligand binding event in a test mixture, the composition comprises a particulate having a surface capable of inducing a surface-enhanced Raman light scattering and having been labeled with a Raman-active label.

According to still another feature of the present invention, there is provided a kit for determining the presence or amount of an analyte in a test sample by monitoring an analyte-mediated ligand binding event in a test mixture, the kit comprises: A Raman-active label; a particulate having a surface capable of inducing a surface-enhanced Raman light scattering; and a specific binding member for the analyte.

BRIEF DESCRIPTION OF THE DRAWINGS

FIG. 8 shows a no-wash immunoassay of standards of human chorionic gonadotrophin (HCG), prepared in pig serum, using gold colloid, a cresyl violet dye or reporter molecule, and a SERRS readout plotted as a function of HCG concentration.

FIG. 9 shows a no-wash immunoassay of standards of human chorionic gonadotrophin (HCG), prepared in human serum using gold colloid, a cresyl violet dye or reporter molecule, and a SERRS readout plotted as a function of HCG concentration.

FIG. 10 shows a no-wash immunoassay of standards of theophylline, prepared in citrate buffer, using silver colloid, an N,N-dimethylanaline-4-azobenzy-4-thiocarbomoyl ethyl aminoethyldisulfide dye or reporter molecule, and a SERRS readout, plotted as a function of theophylline concentration.

FIG. 11 shows a no-wash detection of the inhibition of binding by free biotin, of bovine serum albumin conjugated to both a dye or reporter molecule [dimethylaminoazobenzene (DAB)], and biotin, [abbreviation of complete conjugate is biotin-BSA-DAB], to streptavidin-coated silver colloid, by a SERRS readout plotted as a function of biotin-BSA-DAB concentration.

DETAILED DESCRIPTION OF THE PRESENTLY PREFERRED EMBODIMENTS

Figure 1:
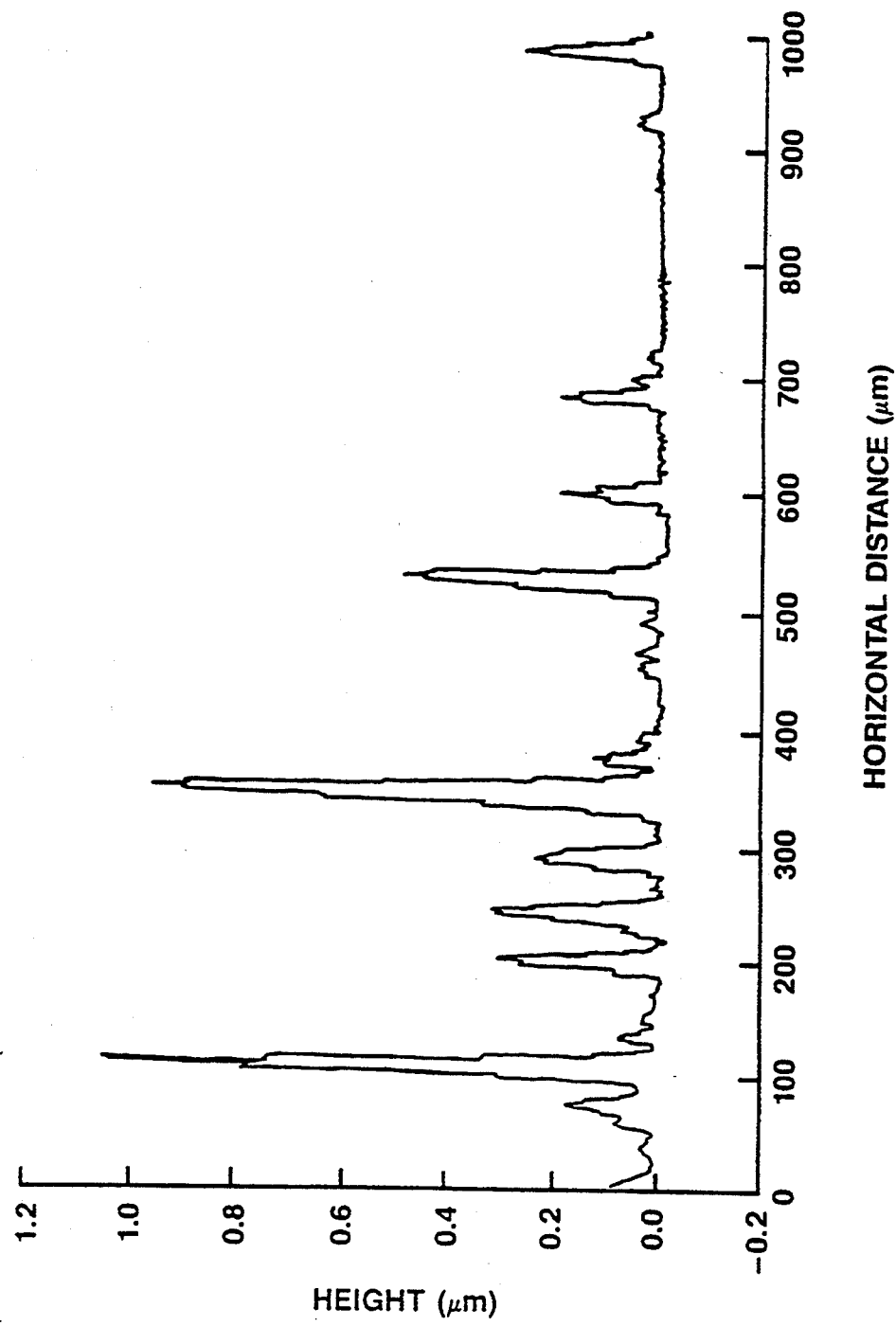
FIG. 1 is a profilometer tracing of an intact, chemically deposited silver film surface.

As previously stated, the present invention involves assay methods, compositions and kits for the determination of the presence or amount of an analyte in a test sample by monitoring differences and changes in the surface-enhanced Raman scattering spectrum of a test mixture which comprises the test sample, a specific binding member, a Raman-active label, and a particulate having a surface capable of inducing surface-enhanced Raman light scattering. It is believed that the presence of an analyte in a dispersed particulate mixture will affect the Raman spectrum obtained from the mixture.

Before proceeding further with the description of various embodiments of the present invention, a number of terms will be defined.

DEFINITIONS

"Analyte," as used herein, is the substance to be detected in the test sample using the present invention. The analyte can be any substance for which there exists a naturally occurring specific binding member (e.g., an antibody) or for which a specific binding member can be prepared, and the analyte can bind to one or more specific binding members in an assay. 37 Analyte" also includes any antigenic substances, haptens, antibodies, and combinations thereof. The analyte can include a protein, a peptide, an amino acid, a carbohydrate, a hormone, a asteroid, a vitamin, a drug including those administered for therapeutic purposes as well as those administered for illicit purposes, a bacterium, a virus, and metabolites of or antibodies to any of the above substances.

"Analyte-analog", as used herein, refers to a substance which cross reacts with an analyte specific binding member although it may do so to a greater or lesser extent than does the analyte itself. The analyte-analog can include a modified analyte as well as a fragmented or synthetic portion of the analyte molecule so long as the analyte analog has at least one epitopic site in common with the analyte of interest.

"Analyte epitope," as used herein, denotes that part of the analyte which contacts one member of the specific ligand binding pair during the specific binding event. That part of the specific binding pair member which contacts the epitope of the analyte during the specific binding event is termed the "paratope."

"Analyte-mediated ligand binding event," as used herein, means a specific binding event between two members of a specific ligand binding pair, the extent of the binding is influenced by the presence, and the amount present, of the analyte. This influence usually occurs because the analyte contains a structure, or epitope, similar to or identical to the structure or epitope contained by one member of the specific ligand binding pair, the recognition of which by the other member of the specific ligand binding pair results in the specific binding event. As a result, the analyte specifically binds to one member of the specific ligand binding pair, thereby preventing it from binding to the other member of the specific ligand binding pair.

"Ancillary Specific binding member," as used herein, is a specific binding member used in addition to the specific binding members of the captured reagent and the indicator reagent and becomes a part of the final binding complex. One or more ancillary specific binding members can be used in an assay. For example, an ancillary specific binding member can be used in an assay where the indicator reagent is capable of binding the ancillary specific binding member which in turn is capable of binding the analyte.

"Agglutination," means a reaction whereby particles suspended in a liquid collect into clumps.

"Associated," as used herein, is the state of two or more molecules and/or particulates being held in close proximity to one another.

"Capture reagent," as used herein, is a specific binding member, capable of binding the analyte or indicator reagent, which can be directly or indirectly attached to a substantially solid material. The solid phase capture reagent complex can be used to separate the bound and unbound components of the assay.

"Conjugate," as used herein, is a substance formed by the chemical coupling of one moiety to another. An example of such species include the reaction product of bovine serum albumin with chemically activated theophylline molecules and the reaction product of chemically activated Raman-active labels with a protein molecule, such as an antibody, or with a ligand, such as biotin.

"Enhancer," as used herein, is any substance which, when present in the test mixture, facilitates a binding, an association, or an agglutination event among particles or soluble substances in a solution or suspension. Enhancers function by changing the pH, ionic, solvent or colligative properties of the liquid medium, or in other ways. Examples of enhancers include, but are not limited to: Salts, such as sodium chloride; any type of buffer preparation which would serve to maintain a desired pH; sugars; and polymers, such as polyethylene glycol.

"Indicator reagent," as used herein comprises a detectable label directly or indirectly attached to a specific binding member or metal surface.

"Intervening molecule," as used herein, is any substance to which both a specific binding pair member and a Raman-active label are attached.

"Particulate," as used herein, is any substance which can be dispersed in a liquid and which will support the phenomenon of a surface-enhanced Raman light scattering (SERS) or surface-enhanced resonance Raman light scattering (SERRS). Examples of particulates include, but are not limited to: Colloids of gold or silver; particles or flakes of gold, silver, copper, or other substances displaying conductance band electrons. As the particle surface participates in the SERS and SERRS effect, flakes or particles of substances not displaying conductance band electrons, which have been coated with a substance which does, also become suitable particulates.

"Radiation," as used herein, is an energy in the form of electromagnetic radiation which, when applied to a test mixture, causes a Raman spectrum to be produced by the Raman-active label therein, and also causes the metal surface to support surface-enhanced Raman light scattering by the Raman-active labels, which become associated with the particulate surface.

"Raman-active label," as used herein, is any substance which produces a detectable Raman spectrum, which is distinguishable from the Raman spectra of other components present, when illuminated with a radiation of the proper wavelength. Other terms for a Raman-active label include dye and reporter molecule.

"SERRS (Surface Enhanced Resonance Raman Scattering)" results when the adsorbate at a SERS active surface is in resonance with the laser excitation wavelength. The resultant enhancement is the product of the resonance and surface enhancement.

"SERS (Surface-Enhanced Raman Scattering)" means the increase in Raman scattering exhibited by certain molecules in proximity to certain metal surfaces.

"Specific binding member," as used herein, is a member of a specific binding pair, i.e., two different molecules where one of the molecules, through chemical or physical means, specifically binds to the second molecule. In addition to antigen and antibody-specific binding pairs, other specific binding pairs include biotin and avidin, carbohydrates and lectins, complementary nucleotide sequences (including probe and captured nucleic acid sequences used in DNA hybridization assays to detect a target nucleic acid sequence), complementary peptide sequences, effector and receptor molecules, enzyme cofactors and enzymes, enzyme inhibitors and enzymes, and the like. Furthermore, specific binding pairs can include members that are analogs of the original specific binding member. For example a derivative or fragment of the analyte, i.e., an analyte-analog, can be used so long as it has at least one epitope in common with the analyte. Immunoreactive specific binding members include antigens, haptens, antibodies, and complexes thereof including those formed by recombinant DNA methods or peptide synthesis.

"Stabilizer," as used herein, is a substance used as an additive with particulates, including colloids, which serve to maintain them in suspension with a reduced tendency to associate. Typical examples of a stabilizer include Tween 20 ™ (sorbitan monooleate nonionic emulsifier); Brij 35 ™, (polyoxyethylene (23) lauryl ether, nonionic emulsifier); Triton ® X-100 , (octylphenoxy polyethoxy ethanol, nonionic emulsifier); polyethylene glycol, and bovine serum albumin.

"Test mixture," as used herein, means a mixture of the test sample and other substances used to apply the present invention for the detection of analyte in the test sample. Examples of these substances include: Specific binding members, ancillary binding members, analyte-analogs, Raman-active labels, buffers, diluents, and particulates with a surface capable of causing a surface-enhanced Raman spectroscopy, and others.

"Test sample," as used herein, means the sample containing the analyte to be detected and assayed using the present invention. The test sample can contain other components besides the analyte, can have the physical attributes of a liquid, or a solid, and can be of any size or volume, including for example, a moving stream of liquid. The test sample can contain any substances other than the analyte as long as the other substances do no interfere with the specific binding of the specific binding member or with the analyte or the analyte-analog. Examples of test samples include, but are not limited to: Serum, plasma, sputum, seminal fluid, urine, other body fluids, and environmental samples such as ground water or waste water, soil extracts and pesticide residues.

Abbreviations
HABA. 2-[4-hydroxyphenylazo]benzoic acid.
DAB. p-dimethylaminoazobenzene.
IgG. Immunoglobulin G.
HTSH. Human thyroid stimulating hormone.
PBS. Phosphate buffered saline
BSA. Bovine Serum Albumin.
TNBSA. 2,4,6-trinitrobenzene sulfonic acid.
DAB-ITC. 4-dimethylaminoazobenzene-4'-isothiocyanate.
DMF. Dimethyl formamide.
I.U. International units.
Biotin-BSA-DAB Conjugate of biotinylated bovine serum albumin with 4-dimethylaminoazobenzene-4'-isothiocyanate
DNP Dinitrophenyl
DNP-BSA Dinitrophenyl Bovine Serum Albumin
DNB Dinitrobenzene

A. ALTERNATIVE PREFERRED EMBODIMENTS

1. Surfaces

Many metallic materials and configurations may be used for the SERS active surface. These materials (for example, silver, gold, copper, platinum etc.) could take the form of flat surfaces (electrodes, strips, slides, etc.) or particulates such as, for example, dispersed colloids, particles, droplets, (i.e. mercury) flakes, or other relatively small, individual structures, or inert support structures for a metal of silica, plastic, glass, paper, or other materials which may be in the form of macroscopically flat or textured (ruled, etched, dimpled, or molded) pieces, slides, strips or spheroids, or fibers which are coated with the active material (e.g., silver, gold, etc.) such that they will support the surface enhancement of Raman scattering described above. The surface or layer giving the enhancement can also be coated with another material (silica, plastic, oxide, etc.) to which the specific binding member is attached.

The presence of photoexcitable surface plasmons is generally considered necessary for surface enhancement. In order for a surface to give a strong SERS effect, its surface plasmons must be localized so that their resident energy is not dispersed. This can be accomplished by dividing the conducting metal (usually silver or gold) into small particles. In practice, the surface of a solid piece of metal can be electrochemically "roughened". As in the examples which follow, silver particles can be precipitated from solution onto a support, or silver can be deposited on a support by evaporation or sputter coating. Silver coated replica gratings also give strong SERS enhancement as do silver coated surfaces which have been textured with bumps or posts, or coated with spheres, then coated with silver.

An attractive surface for SER(R)S based assays particularly suited for the present invention is a particulate in the form of a metal colloid. A metal colloid combines a very strong SER(R)S activity with the advantage of a liquid medium that can readily be handled. The combination of a SER(R)S readout and a colloidal reagent will allow assays to be run in a manner similar to that used for present clinical chemistry analysis.

The metal colloids used in this invention are composed of elemental silver or gold, but are not limited to these metals. For example colloids composed of copper, in addition to other metals, are known to provide for the SERS and SERRS effects. The dispersions of the metals can be prepared by the reduction of dilute salt solutions of the given metals. A variety of reducing agents, such as ascorbate, citrate, borohydride, or hydrogen gas, can be used. The method of preparation can effect the appearance and intensity of the resulting SERS or SERRS spectrum. However, this is not a limiting factor with respect to this invention. Thus, Example 20 demonstrates that SERRS spectra for a 20:1 mixture of two Raman-active labels, or dyes, methylene blue and oxazine 725, adsorbed to separate samples of colloid prepared by citrate reduction and by hydrogen gas reduction can be utilized even though the particulates and the spectra are different.

Colloids made by these reduction methods usually have a negatively charged surface, originating from anions from the reducing agent and its oxidation by-products and possibly metal oxide anions, especially if the reducing agent is removed or in low concentration. The resulting mechanism of colloidal stabilization in these cases is believed to be electrostatic. The details of such mechanism are aptly described in the textbook by Paul C. Hiemenz, *Principles of Colloid and Surface Chemistry*, Marcel Dekker, 1977, Chapters 9–11. Another mechanism of colloidal particle stabilization in suspension is called steric stabilization. Steric stabilization is distinguished from electrostatic stabilization in that the stabilizing moieties are uncharged. These moieties are almost always polymeric in nature and soluble or at least swellable in the continuous, i.e. solvent, phase of the dispersion. In this case, the term "polymeric" can describe synthetic polymer molecules, such as polystyrene or polyethylene oxide, or natural macromolecules, such as proteins, polypeptides, or carbohydrates. In practice, the stabilizing moiety is attached to the surface of the colloidal particle. A simplified explanation of this mechanism can be described for two particles having soluble stabilizing moieties attached to their surfaces. As the two particles approach each other, the concentration of stabilizer increases in the region between the two particles as a function of their separation distance. This also results in an increase in the degree of ordering of the soluble chains in this region. These occurrences are unfavorable from an osmotic and entropic standpoint, hence they reduce the tendency for particles to coalesce or associate in the absence of forces which could overcome these effects. An example of forces which could reduce the effectiveness of steric stabilization is heat, which increases the kinetic energy of the particles and could make the stabilizing moiety less soluble in the suspending medium. An example of this would occur if polyethylene oxide was the stabilizing moiety, anchored to colloidal particles suspended in water. Raising the temperature from room temperature to 50°–70°

C. reduces the solubility of the stabilizer and hence its effectiveness. Addition of a miscible non-solvent suspension would have a similar destabilizing effect. Steric stabilization is not generally sensitive to the ionic strength of the continuous phase, unless it significantly effects the solubility properties of the stabilizer. The topic of steric stabilization is aptly covered in an article by Donald H. Napper, "Steric Stabilization," J. Colloid Interface Sci., 58, 390 1977.

A third mechanism for the stabilization of colloidal particulates is depletion stabilization. This method also uses soluble stabilizing moieties; however, it is not a requirement that they be attached to the surface of the colloidal particle. This type of stabilization may be generated by simply dissolving a non-ionic polymer in the dispersing medium. Stability arises from the depletion of the concentration of free polymeric species between the surfaces of the particles when they approach in close proximity. This process is aptly described in an article by Robert I. Feign and Donald H. Napper, "Depletion Stabilization and Depletion Flocculation," J. Colloid Interface Sci., 75, 525, 1980.

Particulates which are colloidal in nature are most preferred for use in the present invention. They are influenced to varying degrees by each of these stabilizing mechanisms. For example, this invention can use as a component a metal colloid which has attached to or associated with it a Raman-active label, sometimes referred to as "a dye or reporter molecules." These labels can be attached to the metal by simple hydrophobic adsorption or through chemisorption, whereby there is a specific chemical interaction of the metal with a specific functional group on the label. An example of chemisorption to a metal is the interaction of thiol groups with a silver surface, forming silver-sulfur chemisorption bonds. In a metal colloid made under reducing conditions, disulfide moieties can be added to the colloid, and many will be reduced at the metal surface forming thiols, which can subsequently chemisorb to the metal surface. Amino groups also can have an affinity for certain metal surfaces, but it is generally thought to be a weaker interaction than with thiols. When a label is added to a negatively charged metal colloid, and that label contains a group of opposite charge, such as an amino group, charge neutralization can occur resulting in aggregation of the colloid. In these cases, it is desirable to add stabilizers to the dispersing medium whereby they can attach to the particles and provide steric stabilization or remain free in solution and provide depletion stabilization. These stabilization processes are generally insensitive to ionic effects. In practice, commercial non-ionic stabilizers, such as Tween 20 or Brij 35, or natural stabilizers, such as albumin, gamma globulins, or specific gamma globulins which can also serve as specific binding members in immunoassays, can be added prior to the addition of the Raman-active label, or dye.

Calculations by P. K. Aravind, A. Nitzan, and H. Metiu, Surface Sci., 110, 189, 1981, show that the excitation spectrum and local fields for two small (Rayleigh limit) spheres, separated by small distances, are very different from any obvious superposition of the single-sphere behavior. A new resonance appears at lower frequency than that of the single sphere case, and the square of the local field between the spheres is, for silver, an order of magnitude larger than for a single sphere. H. Metiu in his review, entitled, "Surface Enhanced Spectroscopy" in Progress in Surface Science, Vol. 17, pp. 153-320, 1984, states, on page 238, that emission enhancement is also expected to increase by a factor of 10 in this case and the enhanced Raman spectrum of a molecule located between two silver spheres could be a hundred times larger than that of a molecule located near a single sphere. He further points out that particle coagulation can alter radically the electrodynamic behavior of the colloidal system and it should be avoided in measurements which intend to provide a test of single-sphere theory.

In the present study, it was found that the SERRS spectra of Raman-active labels located near or associated with the surface of metal colloids associated with a specific binding member was affected by the addition of its complementary specific binding member. It is thus possible to speculate that the electrodynamic behavior of the suspensions described in the assay examples which follow are changed in a way detectable by the SERRS behavior of the dye label. This may be due to the association of colloidal particles, modulated by the interaction of an analyte with its binding member which is immobilized on the colloid surfaces.

2. Attachment of Specific Binding Members to SERS-Active Surfaces

A specific binding member can be attached to the SERS-active surface by direct adsorption, attachment through an intervening molecule or a linker arm, covalently attached to the specific binding member, or by the covalent attachment of the specific binding member to a coating on the SERS-active surface directly or through a linker arm or by intercalation of the distal portion of a linker arm into the enhancing surface.

3. Raman-Active Labels,

The Raman-active labels, can be any one of a number of molecules with distinctive Raman scattering patterns. Unlike the enzymes used in enzyme immunoassays, these label species can be stable, simple, inexpensive molecules which can be chemically modified as required.

The following attributes enhance the effectiveness of the label in this application:
(a) A strong absorption band in the vicinity of the laser excitation wavelength (extinction coefficient near $10^4$);
(b) A functional group which will enable covalent attachment to a specific binding member;
(c) Photostability;
(d) Sufficient surface and resonance enhancement to allow detection limits in the subnanogram range;
(e) Minimal interference in the binding interaction between the labeled and unlabeled specific binding members;
(f) Minimal exhibition of strong fluorescence emission at the excitation-wave length used;
(g) A relatively simple scattering pattern with a few intense peaks; and/or
(h) Labels with scattering patterns which do not interfere with each other so several indicator molecules may be analyzed simultaneously.

The following is a listing of some, but not all potential candidates for these Raman-active label: 4-(4-Aminophenylazo)phenylarsonic acid monosodium salt, arsenazo I, basic fuchsin, Chicago sky blue, direct red 81, disperse orange 3, HABA (2-(4-hydroxyphenylazo)-benzoic acid), erythrosin B, trypan blue, ponceau S, ponceau SS, 1,5-difluoro-2,4-dinitrobenzene, cresyl violet and p-dimethylaminoazobenzene. The chosen labels may be covalently attached to the specific binding members of interest or attached or associated with.

4. Excitation Sources

In the preferred embodiment, a laser serves as the excitation source. The laser may be of an inexpensive type such as a helium-neon or diode laser. An operating lifetime of such lasers may be in excess of 50,000 hours.

In one embodiment, a diode laser is used to excite at or at the near IR spectrum, minimizing fluorescence interference. The excitation sources used need not necessarily be monochromatic and they also need not necessarily have to be of high intensity. Lamps may also be used.

The SERS effect can be excited by direct illumination of the surface or by evanescent waves from a waveguide beneath the plasmon-active surface.

5. Conjugates

Several different conjugates could be prepared from specific binding members having different specificities, each type with a different Raman active label having a distinctive scattering pattern. Mixing these conjugates in an assay would allow the simultaneous analysis of several different analytes in the same sample.

6. Detection

Several methods are available for detecting Raman scattering. These generally can be used with different types of spectrometers. In SERS, the primary measurement is one of light scattering intensity at particular wavelengths. SERS requires measuring wavelength-shifted scattering intensity in the presence of an intense background from the excitation beam. The use of a Raman-active substance having a large Stokes shift simplifies this measurement.

Several concepts for further simplifying the readout instrument have been proposed. These include the use of wavelength selective mirrors, filters or holographic optical elements for scattered light collection.

Neither the angle of the incident light beam to the surface nor the position of the detector is critical using SERS. With flat surfaces positioning the surface of the laser beam at 60 degrees to the normal is commonly done and detection at either 90 degrees or 180 degrees to the beam are standard. SERS excitation can be performed in the near infrared range which would suppress intrinsic sample fluorescence. It may also be possible to perform SERS-based ligand binding assays using evanescent waves produced by optical waveguides.

No signal development time is required as readout begins immediately upon illumination and data can be collected for as long as desired without decay of signal unless the excitation light is extremely intense and chemical changes occur. The signal cannot overdevelop as in systems dependent on optical absorbance. Unlike fluorescent readout systems, SERS reporter groups will not self-quench so the signal can be enhanced by increasing the number of Raman reporter groups on the probe molecule. Fluorescent molecules near the SERS-active surface will actually be surface-quenched.

7. Instrumentation

The present invention is adaptable for use as an automatic analyzer. Since the instrument would monitor discrete Stokes shifted spectral lines, the need for an elaborate monochromator system is not necessary. Recent advances in state-of-the-art optics technology, such as holographic optical elements, allow the design of a suitable spectrometer with cost and complexity below that of the laboratory grade device.

Optical readout energies as a result of SERS are above that which require ultra-sensitive photon counting devices. In fact, some SERRS spectrometers now in use incorporate silicon photodiode detectors. The optical efficiency of a typical monochromator used in a laboratory grade spectrometer is less than 10%. The advances in optical materials and components mentioned above should make possible two to three-fold increases in optical efficiency for a simple spectrometer dedicated to only a few specific spectral lines. This also addresses one of the previously major concerns, blocking of the Rayleigh scattering line. With blocking capabilities of newer filters on the order of $10^{-9}$, substitution of filters for one or more stages of the typical monochrometer system should be possible with significant cost savings.

8. Devices for Analysis

The general technology for analyzing an analyte in a test sample by means of a chromatographic binding assay is known in the art. For example, Deutsch et al. describe chromatographic test strip device in U.S. Pat. Nos. 4,094,647, 4,235,601 and 4,361,537. These references are herein incorporated by reference. Variations on the Deutsch el al. device have been disclosed in U.S. Pat. Nos. 4,366,241 and 4,186,146. Zuk et al., "Enzyme Immunochromatography, A quantitative Imunoassay Requiring No Instrumentation," Clin. Chem., 31, 1144, 1985, further describe the assay principle. Also of interest are U.S. Pat. Nos. 4,298,688; 4,517,288; 4,740,468; and 4,366,241; E.P. Publication Nos. 88,636; 259,157; and 267,006.

B. EXAMPLES

Example 1

Preparation Of Silver Surfaces

Support surfaces—Supports for the silver films were either flat, frosted glass pieces cut from microscope slides or quartz pieces cut from 4 in. ×4 in. ×20 mil. quartz substrates (General Electric Type 124).

Chemical deposition—Silver was deposited on support surfaces by chemical reduction of silver nitrate as previously described by Ni and Cotton. Anal. Chem. 58, 3159, 1986. Tollens reagent was used to deposit the silver. Tollen's reagent was prepared in a small beaker by adding about 10 drops of fresh 5% NaOH solution to 10 mL of 2-3% $AgNO_3$ solution, whereupon a dark-brown AgOH precipitate is formed. This step was followed by dropwise addition of concentrated $NH_4OH$, at which point the precipitate redissolves. The beaker containing the clear Tollen's reagent was then placed in an ice bath. The frosted slides, which had been cleaned with nitric acid and distilled water, were placed into a Teflon frame, which could accommodate up to 15 slides, and placed into the Tollen's reagent. Three milliliters of 10% D-glucose was added to the solution with careful swirling to ensure mixing. The beaker was then removed from the ice bath and the solution allowed to reach room temperature. The beaker was placed into a water bath (55° C.) for 1 min followed by sonication for 1 min (Branson Sonicator, Model B22-4, 125 W). Finally, the silver-coated slides were rinsed several times with distilled water and again sonicated in distilled water for 30 sec. The slides were then stored in distilled water for several hours prior to exposure to the adsorbate solution. By use of this procedure, slides were found to be stable in distilled water for up to 1 week.

The surfaces were yellow by transmitted light and demonstrated a coarse, granular appearance by scanning electron microscopy. A profilometer probe traversing the surface revealed many prominences, some approaching $10^3$ nm in height (FIG. 1). A cross section of the silver layer generated by scratching the surface with a stylus revealed it to be composed of partially fused spheroids approximately 100 nm in diameter. The step produced by scratching the silver off the substrate was found to be approximately 130 nm thick by profilometry.

Sputter coating—Quartz pieces were coated with a 75 Å layer of silver by sputter coating using a Perkin-Elmer Randex Model 2400-85A while being rotated at 2.25 rpm for 4.5 min at a distance of 6.75 cm from the silver target. A forward power of 200 W and an argon flow rate of 12.25 cc/min were used. The silver film was transparent and blue by transmitted light. Scanning electron microscopy at a 2500-fold enlargement showed a fine-grained featureless surface.

Silver electrodes—Silver electrodes were prepared as previously described by Ni and Cotton, J. Raman Spectroscopy, 19, 429, 1988. They were constructed by sealing a flattened silver wire into a glass tube with Torr Seal. The exposed surface was rectangular with dimensions of approximately 2×10 mm. The electrode was polished with a slurry of 0.3 µm alumina in water on a mechanical polishing wheel. it was then rinsed and sonicated in distilled water to remove any alumina which might have adhered to the surface. This step was followed by roughening the electrode by an oxidation-reduction cycle (ORC), consisting of a double potential step from an initial potential of $-550$ mV to $+500$ mV and back to $-550$ mV in 0.1M $Na_2SO_4$ solution. An Ag—AgCl electrode was used as the reference electrode and a Pt electrode as the auxiliary electrode. The total charge passed during the oxidation step was equivalent to 25 mC $cm^{-2}$.

Silver colloids—Silver colloids were prepared by a modification of the procedure of Lee and Meisel, J. Phys. Chem. 86, 3391, 1982. An aliquot of 90 mg of silver nitrate was dissolved in 500 ml of distilled water and brought to boiling. A 10 ml solution of 1% sodium citrate was added all at once and the solution was stirred for 45 minutes, during which the silver colloid formed. The colloid was cooled to room temperature and stored for use without further purification. Typical particle sizes resulting from such preparations ranged from 20 to 80 nm.

Example 2

Preparation of Dye-Antibody Conjugates

Antibody (2 mg) was dissolved in 2 ml of 1% NaHCO$_3$ pH 8.6, and a 20-ul aliquot of a solution of 1 mg/ml 4-dimethylaminoazobenzene-4'-isothiocyanate in dimethylformamide (DMF) added. The mixture was stirred overnight, then desalted on a Sephadex G-25 (coarse) column (1×30 cm). The ultraviolet-and visible spectrum of the conjugate was compared to that of DAB and antibody alone, to determine the degree of substitution. An erythrosin-antibody conjugate was prepared the same way, except the concentration of the erythrosin-isothiocyanate in DMF was 2.5 mg/ml.

Example 3

Conjugation Of DINITROPHENYL (DNP) Groups To Bovine Serum Albumin To Form a DNP-BSA Conjugate A solution of 2 ml of 2,4-dinitrofluorobenzene in 150 ml of ethanol was mixed with a solution of 200 mg of bovine serum albumin and 10 g $Na_2CO_3$ in 100 ml distilled water. The mixture was stirred for 24 h and centrifuged at 3000×g for 20 min to remove precipitated material and the supernate was dialyzed against 6 liters of phosphate-buffered saline (PBS) for 23 h, then against two changes of 2 liters of PBS for 6 h each, and finally against two changes of 2 liters of distilled water, 6 h each. Dialysis was carried out at room temperature with 0.02% sodium azide present in all solutions, except the final 2 liters of water. The contents of the dialysis bag were then lyophilized to dryness, yielding 136 mg. A sample was compressed into a potassium bromide pellet and its infrared spectrum recorded on a Nicolet 60 SX FT infrared spectrometer. A strong vibrational band at 1340 $cm^{-1}$ not inherent to native BSA, indicated introduction of nitro groups (data not shown). The degree of substitution of the BSA was determined by comparing the degree to which BSA and the nitro-BSA conjugate could be derivatized with 2,4,6-trinitro-benzene-sulfonic acid (TNBSA). After reaction with TNBSA, the average absorbance at 330 nm of a 1 mg/ml solution of native BSA increased from 0 to 1.5 as the result of the derivatization of free amino groups. The same concentration of the DNP-BSA conjugate had an initial absorbance at 330 nm of 1.2 (from the DNP groups) which did not increase after incubation with the TNBSA reagent. It can be concluded that essentially all the available amino groups in the DNP-BSA conjugate had been derivatized with DNP by the Sanger's reagent.

Example 4

Generation of SERS Spectra by DNP-BSA Conjugate Absorbed to Silver Films

Figure 2:
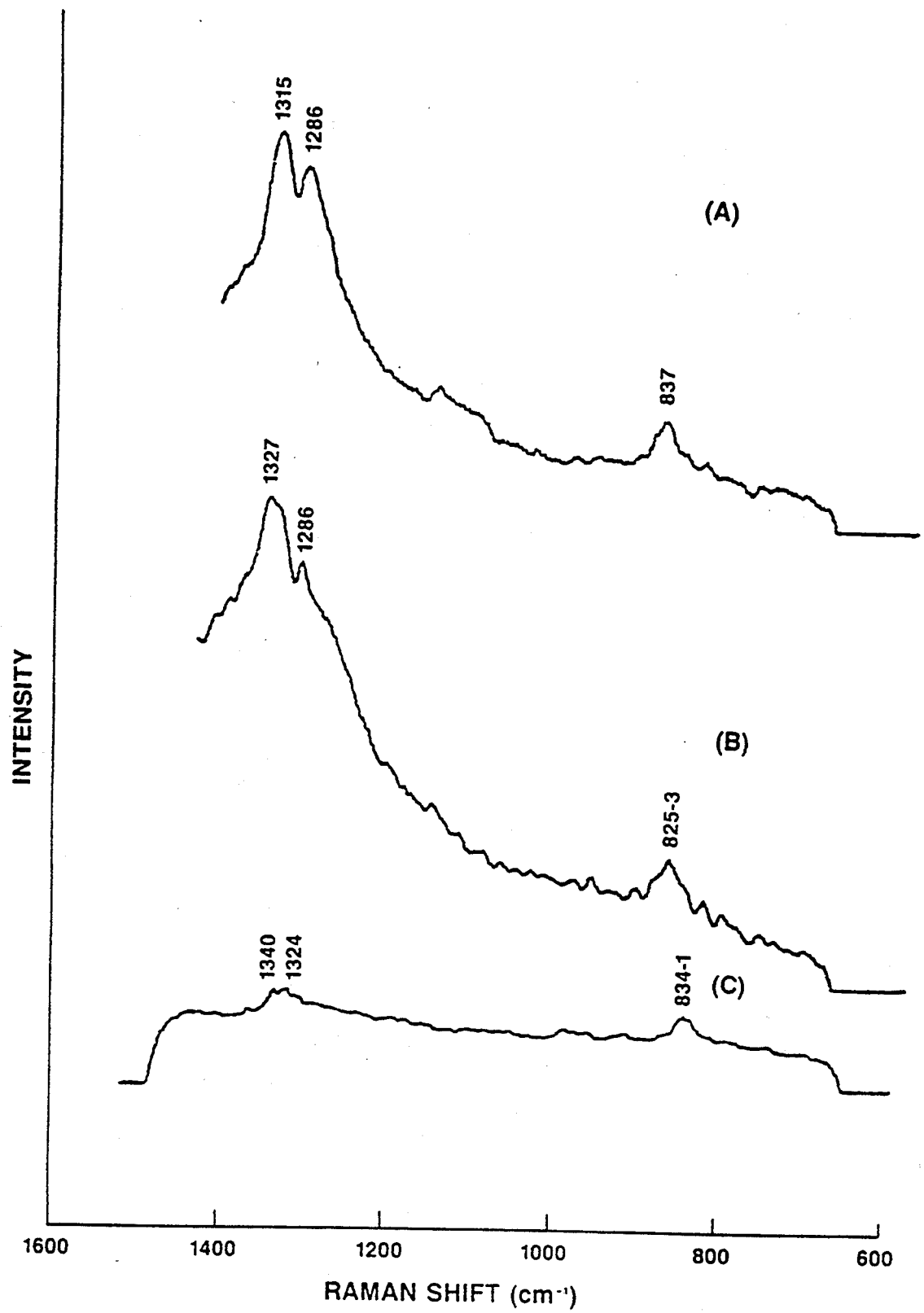
FIG. 2 is Raman spectra of (A) 2,4-dinitrobenzene solution, $10^{-3}$M, in the presence of chemically deposited silver film, (B) 2,4-dinitrophenyl-BSA conjugate, $10^{-7}$M with respect to DNP moieties, in the presence of a chemically deposited silver film, and (C) 2,4-dinitrobenzene, $10^{-3}$M, in the absence of a silver film (ordinate expanded fourfold relative to A and B to enhance features). Spectra acquisition conditions: acquisition time, 19 sec; power, 41 mW; excitation wavelength, 457.9 nm.

Freshly prepared silver-coated slides (chemically deposited) were incubated in buffer (pH 8.6) containing free dinitrobenzene (DNB) (FIG. 2A) or DNP-BSA conjugate (FIG. 2B), and SERS spectra obtained in both cases. Similar peak intensities were observed with free DNB at $10^{-3}$M and DNP-BSA at $10^{-7}$M with respect to DNP moieties ($2 \times 10^{-9}$ BSA), respectively. The four orders of magnitude difference in the specific intensity of surface-enhanced Raman light scatter observed between the free DNB and the DNP moieties of the DNP-BSA conjugate represents the greater ability of the latter to adsorb to the island film surface, thereby enabling its DNP moieties to display the SERS enhancement. A $10^{-3}$ m solution of DNB in the absence of an island film gave a very weak Raman spectrum (FIG. 2C).

Example 5

Use of a Raman-Active Dye to Demonstrate Surface—Enhanced Resonance Raman Spectroscopy An avidin molecule will bind four molecules of the dye HABA, with an affinity constant of $K_a = 5.8 \times 10^6$ liter/mol at pH 7.0. Because this dye has a major spectral absorption at a wavelength which can be used to excite Raman light scattering (absorption maximum=495 nm when bound to avidin at pH 7), it is capable of SERRS.

Figure 3:
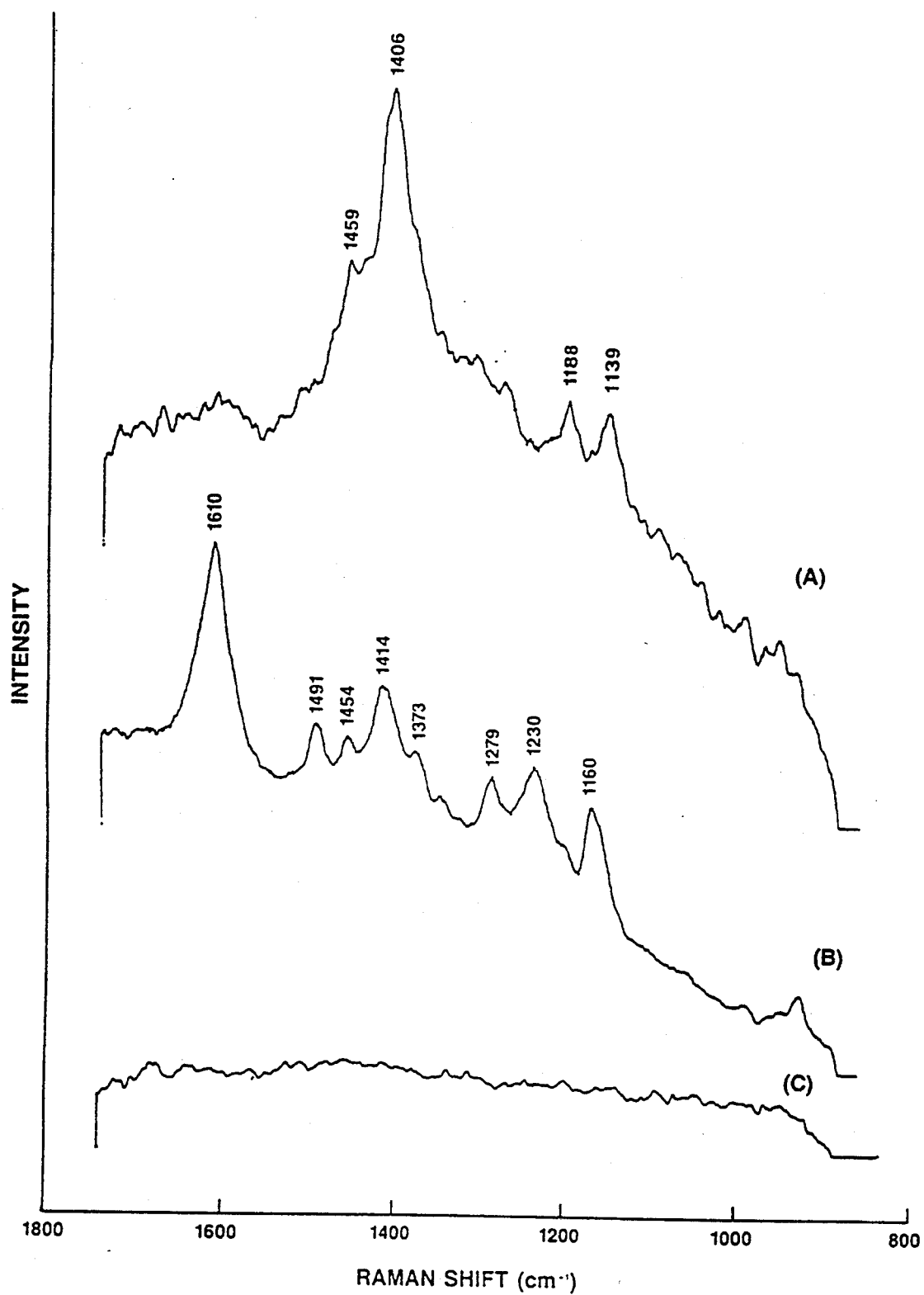
FIG. 3 is a SERRS spectrum obtained from a chemically deposited silver film incubated in (A) a 3 mM solution of HABA and (B) a $2.5 \times 10^{-5}$M solution of avidin subsequently made 0.3 mM in HABA. No discernible spectrum was observed in this region from surface absorbed avidin in the absence of HABA (C). Spectra acquisition conditions: acquisition time, 100 sec. power, 50 MW; excitation wavelength, 457.9 nm.

Chemically deposited silver films, with and without prior coating with avidin, were incubated in a 3 mm solution of HABA. The films were then removed from the HABA solution and washed with PBS, and their Raman spectra taken. FIG. 3A is the spectrum obtained when HABA is adsorbed directly onto the surface of a silver film. A single major peak of light scattering intensity is observed at 1406 wavenumbers, with a shoulder at 1459 and minor peaks at 1188 and 1139 cm$^{-1}$. The spectrum shown in FIG. 3B was obtained when a silver film was first incubated for 20 min at room temperature in a $2.5 \times 10^{-5}$M solution of avidin, then HABA added to a final concentration of approximately 0.3 mM, and incubation continued for an additional 20 min. Under these conditions, the major peak of Raman scattering intensity is observed at 1610 cm$^{-1}$ with several smaller peaks appearing between 1160 and 1491 cm$^{-1}$ The large peak at 1406 cm$^{-1}$ seen in the absence of avidin, is no longer observed. In the absence of HABA, an avidin-coated silver film gave no discernible spectrum in this region (FIG. 3C).

Example 6

Dye-Antibody Conjugates and Raman Readout in a Sandwich Immunoassay

Silver electrodes were incubated at 37° C. for 1 h in 1 ml aliquots of a solution of 20 µg/ml anti-TSH antibody in 1% NAHCO$_3$, pH 8.6, and then over-coated for an additional hour in 1% BSA in PBS at 37° C. The films were then incubated for 1 h at 37° C. in the 0, 4, 10, 25 or 60 µIU/ml TSH antigen standards from the Abbott TSH EIA kit, Abbott No. 6207. After being washed three times with PBS, the films were transferred to test tubes containing 1 ml of the DAB-anti-TSH antibody conjugate at a concentration of 40 µg/ml, incubated for an additional hour at 37° C., washed again, and the SERRS spectra obtained.

Figure 4:
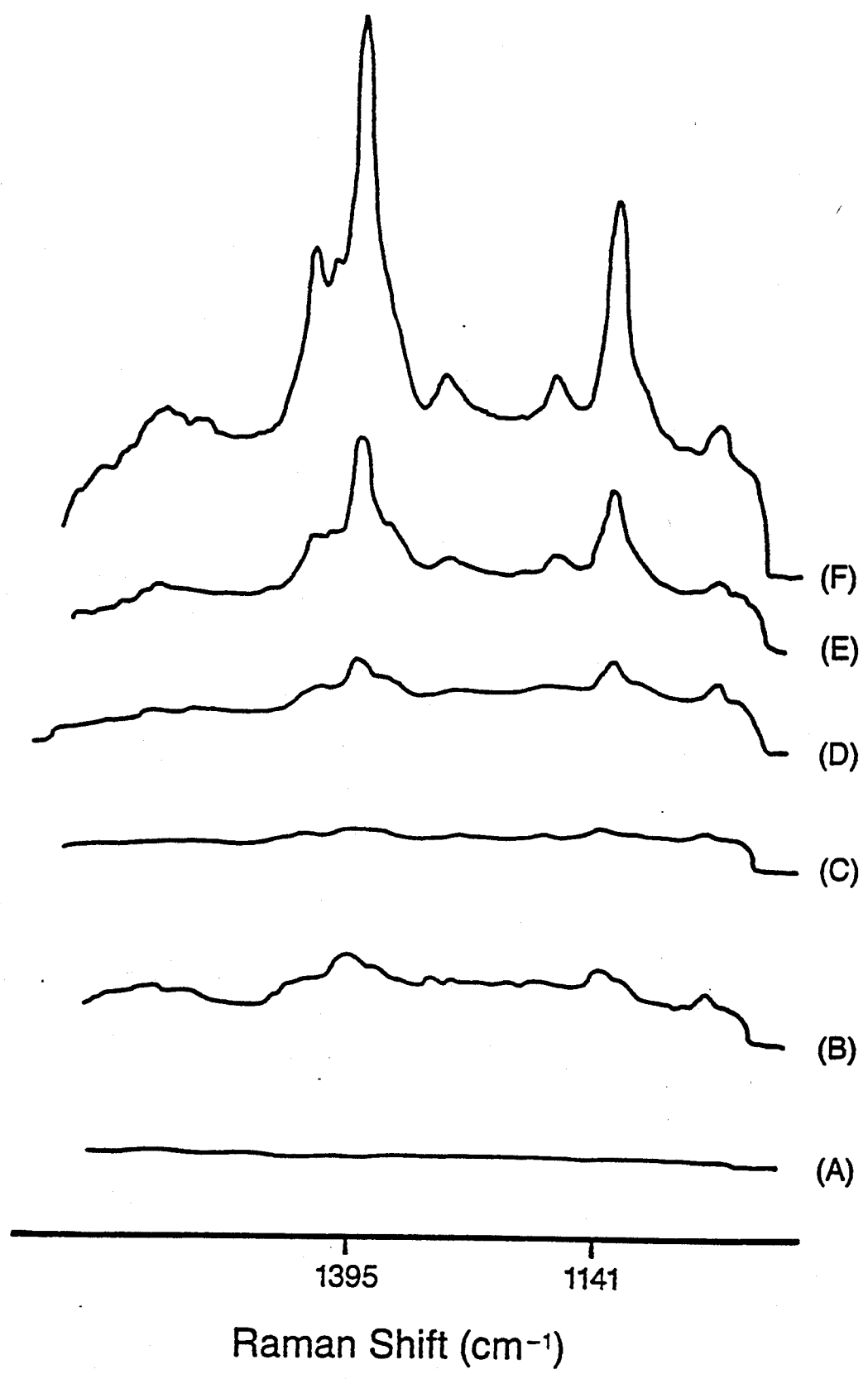
FIG. 4 is a combined plot of typical SERRS spectra obtained in a "sandwich" immunoassay for TSH antigen using a DAB-anti-TSH antibody conjugate. Silver electrodes coated with anti-TSH capture antibody were incubated with various concentrations of TSH antigen and then transferred to a 40 µg/ml solution of DAB-anti-TSH antibody conjugate. (A) SERRS spectrum of a 40 µg/ml solution of DAB-anti-TSH antibody conjugate in the absence of a silver surface. Plots (B), (C), (D), (E), and (F) show spectra obtained by incubating capture antibody-coated electrodes in solutions containing 0, 4, 10, 25 and 60 µIU of TSH antigen, respectively, followed by transfer to a 40 µg/ml solution of DAB-anti-TSH antibody conjugate.
Figure 5:
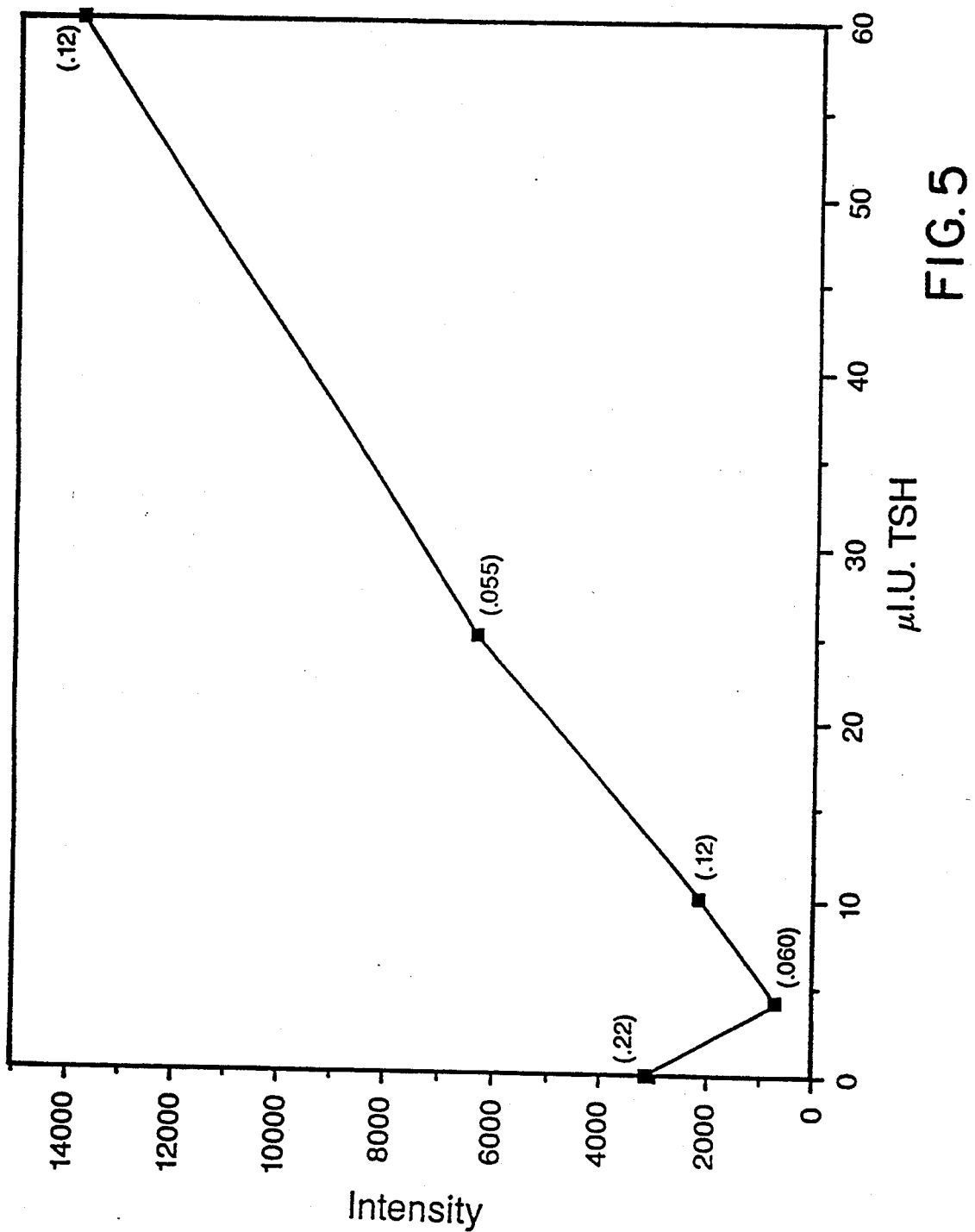
FIG. 5 is a plot of average SERRS intensity at 1410 cm$^{-1}$ as a function of TSH antigen concentration for known TSH standards. Values were obtained at five different places on the silver electrode and averaged. One electrode was used for each concentration of TSH antigen measured. Numbers in parentheses are the coefficients of variation (standard deviation/mean) for each concentration of analyte measured.
Figure 6:
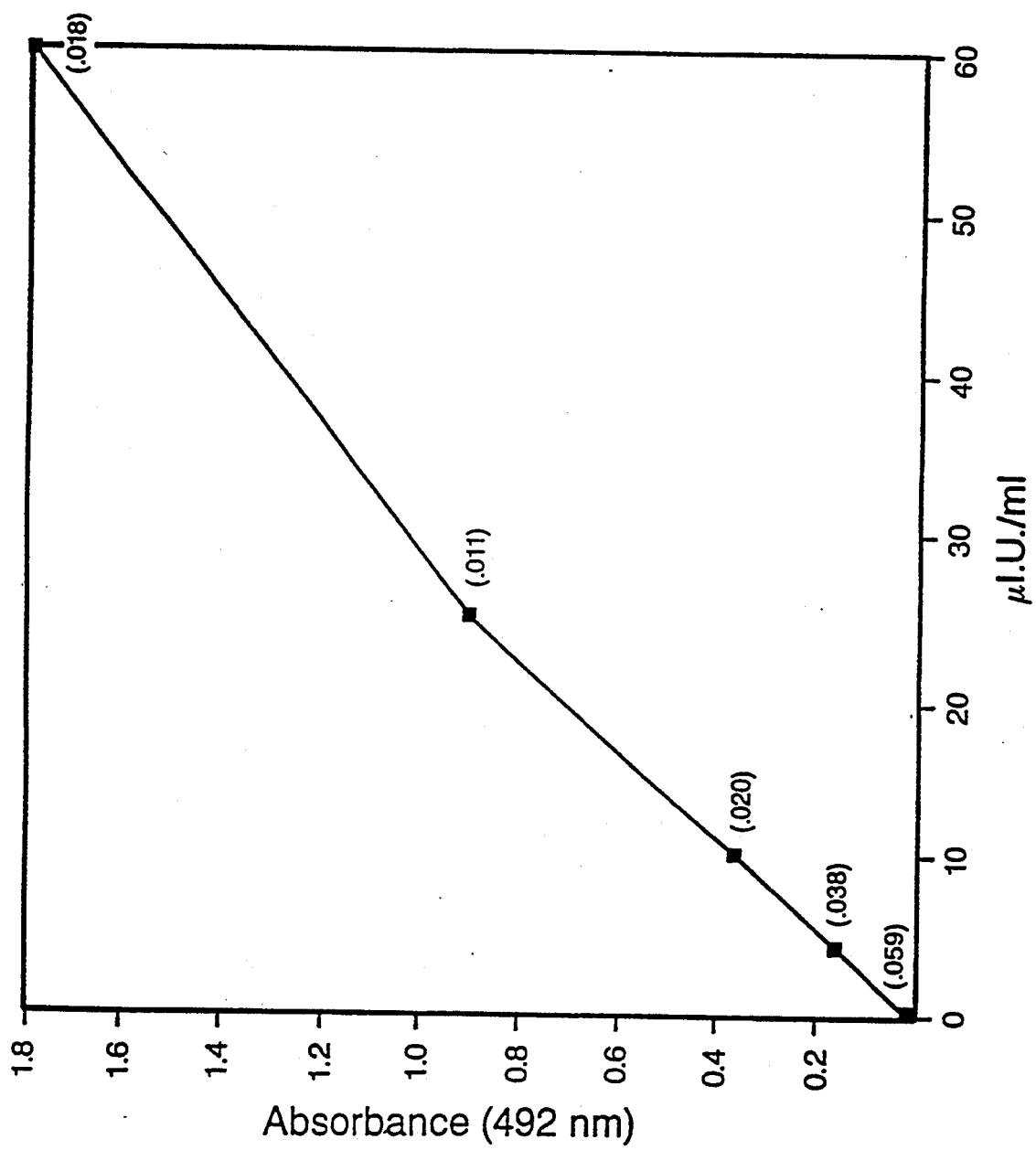
FIG. 6 is absorbance (492 nm) vs. TSH antigen concentration obtained using reagents from a commercial enzyme immunoassay kit (Abbott Labs No. 6207). Each data point represents the average of four determinations. The numbers in parentheses are the coefficients of variations (standard deviation/mean) for each concentration of TSH antigen measured.

SERRS spectra were obtained at five different places along each electrode and the results recorded. A combined plot of typical spectra obtained is shown in FIG. 4 for the five concentrations of TSH antigen studied. The averaged peak intensities at 1151 cm$^{-1}$ were used to generate a signal vs. concentration curve (FIG. 5). The same standards were also assayed using a modified commercial enzyme immunoassay (Abbott No. 6207, FIG. 6). Comparison of the two plots shows that the response obtained using the SERRS readout is similar to that given by the enzyme immunoassay, except for an anomalously high value for the zero antigen standard. This high zero reading was consistent upon reassay and must reflect a difference in composition between the zero standard and the other standards which does not effect results obtained by enzyme immunoassay.

Example 7

No Wash Immunoassay

A solution of 1% ascorbic acid was added to a silver colloid (approximately 0.02% solids, 30±5 nm particle diameter) to a final concentration of 1 mM. To individual 3.0 ml aliquots of colloid solution were added 0.015 ml each of anti-human thyroid stimulating hormone antibody (1 mg/ml in phosphate buffered saline). The pH of the antibody-coated sol was then adjusted to 7.4 with phosphate buffer.

To one sample of antibody-coated sol was added 0.015 ml of 60 µl.U./ml human thyroid stimulating hormone (HTSH) standard. To the second sample was added 0.015 ml of 0 µl.U./ml HTSH standard. Both standards were contained in a pig serum matrix. An amount of 0.015 ml of p-dimethylaminoazobenzene-anti-TSH (DAB-ANTI-TSH) conjugate were added to each sample and incubated. After 20 minutes the surface-enhanced Raman spectra were recorded. The results showed approximately 2 times as intense a signal at a Raman shift of 1403 cm$^{-1}$, the strongest peak in the spectrum of the DAB dye, for the sample with the 60 µl.U./ml HTSH compared to the 0 µl.U./ml sample.

Example 8

Demonstration of SERS on Protein-Dye Conjugates using Near Infrared Excitation

Figure 7:
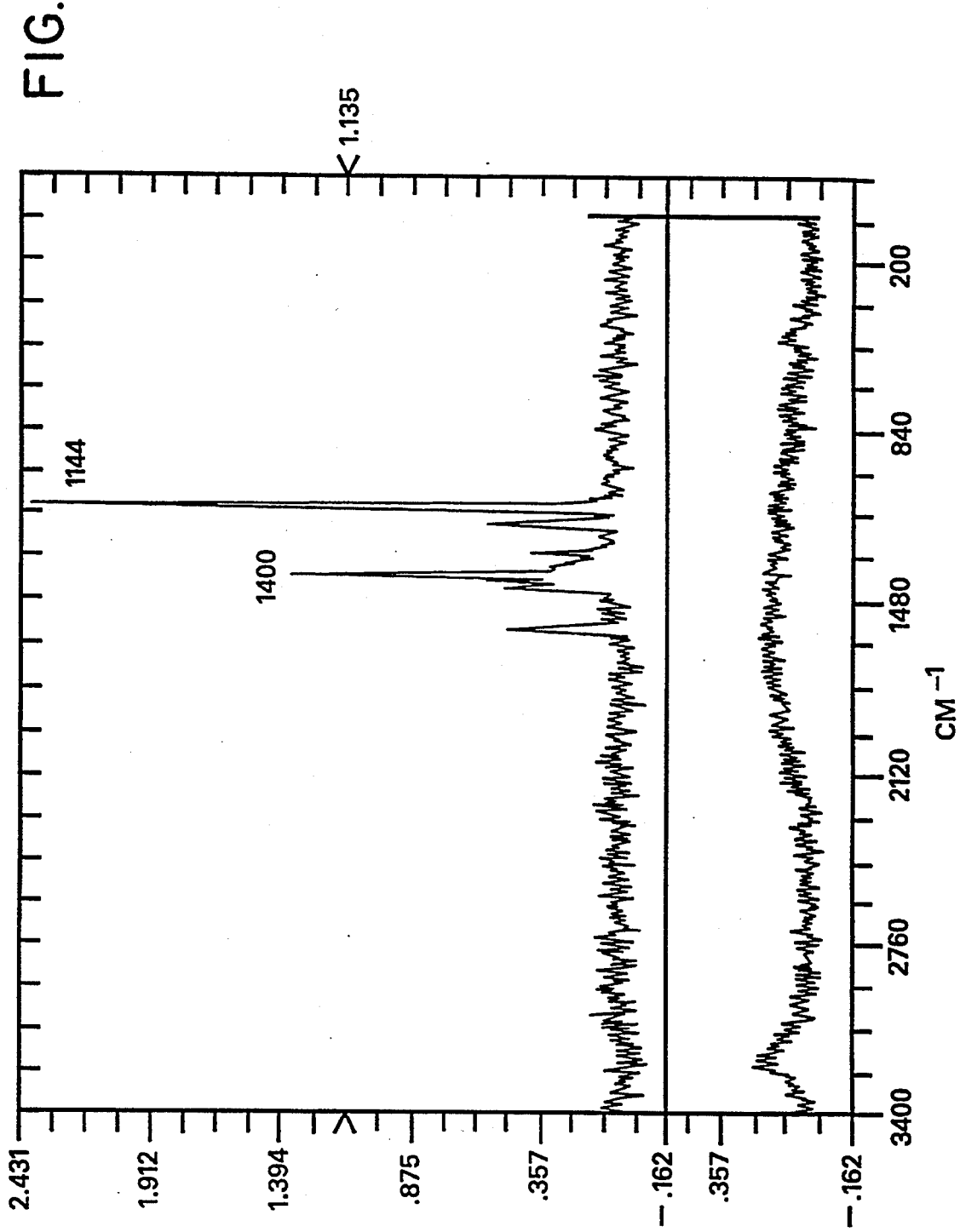
FIG. 7 is a SERS spectra using near IR excitation for (A) spectrum of a blank silver film determined separately and added to a solution state spectrum done in the absence of a silver surface, of the p-dimethylamino-azobenzene bovine serum albumin conjugate at 20 mg/ml, (B) spectrum obtained by immersing the blank silver film in the aforementioned solution of the p-dimethylaminoazobenzene bovine serum albumin conjugate.

A chemically deposited silver film was immersed in water in a cuvette and the SERS spectrum was recorded using a Bomem Raman spectrometer using excitation from a Nd:Yag laser at 1.06 nm. There was essentially no spectrum that was discernable from random noise. An aqueous solution of a p-dimethylaminoazobenzene-bovine serum albumin conjugate at 20 mg/ml was also scanned, but in the absence of any silver surface. Once again virtually no usable spectrum was distinguishable from the noise at the concentration used. This data was summed and plotted, and served as the blank for the experiment (FIG. 7A). The silver film used in the blank above was then added to the cuvette containing the dye-protein conjugate and the Raman spectrum taken. The data from the blank runs were subtracted giving the resultant SERS spectrum of the dye (FIG. 7B), which showed strong Raman scattering at Raman shifts of 1400 and 1144 cm$^{-1}$.

Example 9

Preparation of Gold Colloid

A clean 1000 ml round bottom flask was washed with (laboratory glassware detergents) soap and rinsed several times with distilled water. The flask was equipped with a magnetic stirrer and a heating mantle. Hydrogen tetrachloroaurate trihydrate (0.058 g) was dissolved in 5 ml of distilled water. The flask was charged with 500 ml of distilled water and was heated to boiling with stirring. The gold salt solution was added to the flask, followed by 3.8 ml of 1.0% sodium citrate solution. Colloid formation was evident after 20 seconds by a change in color from a light yellow solution transitioning through the following colors: purple-to-gray-to-red, and finally lavender-red. No aggregation was visible to the eye. Electron microscopy of samples made by this procedure yielded particles in the 50–60 nm diameter range.

Example 10

Preparation Of An Anti-HCG Gold Colloid SERRS Reagent (Method 1)

Gold colloid (10.0 ml) was adjusted to pH 6.5–7.0 using 0.02M K$_2$CO$_3$. Two antibodies, one mouse monoclonal and the other polyclonal, which specifically bind to human chorionic gonadotropin (HCG) (the analyte of interest in tests using this reagent) were diluted separately in 5 mM NaCl to 1.00 mg/ml. Gold colloid was aliquoted into two 5 ml samples. To one sample was added 25 µl of polyclonal antibody and to the other samples was added 25 µl of monoclonal antibody. The individual colloid samples were mixed by gentle shaking and were then incubated at room temperature for 10 min. After incubation, 100 µl of polyethylene glycol (carbowax 20M) solution at 10 g/l was added to each 5 ml aliquot and they were incubated for 1 hour at room temperature. After incubation the gold colloids were transferred to 1.7 ml microfuge tubes and centrifuged for 5 minutes at approximately 5000×g, forming distinct pellets. The supernatant was removed and replaced with 0.2 g/l carbowax 20M. The pellet was redispersed with gentle shaking. This centrifugation and washing was repeated for a total of 3 times. The sols containing like antibody were recombined. To obtain a colloidal reagent for use in the assay by Surface-Enhanced Raman Scattering Spectroscopy, equal volumes of the two colloids (polyclonal-coated and monoclonal-coated) were mixed together before use.

Example 11

Preparation Of An Anti-HCG Gold Colloid SERRS Reagent (Method 2)

Gold colloid (30.0 ml) was adjusted to pH 6.5–7.0 using 0.02M $K_2CO_3$. Two antibodies, one mouse monoclonal and the other polyclonal, which specifically bind to human chorionic gonadotropin (HCG) (the analyte of interest in tests using this reagent) were diluted separately. The polyclonal antibody was diluted in 0.01 citrate buffer, pH 5.3 at a concentration of 0.250 µg/ml. The monoclonal antibody was diluted into 5 mM NaCl, pH 7.0, at a concentration of 0.250 µg/ml. Gold sol was aliquoted into two 15 ml samples. To one sample was added 150 µl of polyclonal antibody and to the other sample was added 300 µl of monoclonal antibody. Each colloid was mixed by gentle shaking and were then incubated at room temperature for 10 min. After incubation, 300 µl of polyethylene glycol (carbowax 20M) solution at 10 g/l in 5 mM NaCl, pH 7.2, was added to each 15 ml aliquot and they were incubated for 1 hour at room temperature. After incubation the gold colloids were added to 1.7 ml microfuge tubes and centrifuged for 5 minutes at approximately 5000×g forming distinct pellets. The supernatants were removed and replaced with carbowax 20M (10 g/l in 5 mM NaCl, pH 7.2). The pellets was redispersed with gentle shaking. The centrifugation was repeated a second time, but this time, the supernatant was replaced with carbowax 20M at 0.2 g/l, 86 mM NaCl, pH 7.2. The colloids containing like antibody were recombined. To obtain a colloidal reagent for use in the assay by Surface-Enhanced Raman Scattering Spectroscopy, equal volumes of the two colloids (polyclonal-coated and monoclonal-coated) were mixed together before use.

Example 12

SERRS No-Wash Immunoassay For HCG.

HCG standards were made up in pig serum at 0, 31, 63, 125, 250, 500, 1000, and 2000 ml.U./ml. This dilution procedure involved adding small volumes of concentrated HCG to large volumes of serum, hence the total amount of protein in each sample was the same, but varied only in the level of HCG present. Microtiter wells were used as mixing chambers for the test and to each well was added 10 µl of HCG standard at a given concentration. This was followed by 200 µl of gold colloid immunoreagent. To run the test, the mixture was removed from the well and added to a mini-test tube, and 5 µl of an aqueous cresyl violet solution (1.35 µg/ml) was added. The suspension was mixed by vortexing and read immediately by recording the surface-enhanced Raman spectrum originating from the cresyl violet dye. The strongest peak was at a Raman shift of 591 $cm^{-1}$ from the excitation wavelength of 647.1 nm. The measured the intensity of that peak decreased as a function of the HCG concentration, allowing a standard assay curve to be generated as shown in FIG. 8.

Example 13

SERRS No-Wash Immunoassay For HCG.

Example 12 was repeated with the following changes:

1. The HCG standards were made up in human serum instead of pig serum.
2. 5 µl Of each standard was added per well instead of 10 µl.

The standard assay curve is shown in FIG. 9.

Example 14

Preparation of Silver Colloid

A 1000 ml pyrex round bottomed flask and glass stirrer assembly were pre-cleaned by soaking overnight in aqua regia. The stirrer consisted of a glass shaft with a 1 inch diameter glass ring fused to the end. Freely attached to this ring were two additional 1 inch diameter rings arranged in a fashion similar to keys on a key chain, and these two rings served as "paddles". The flask and stirrer were rinsed 10 times with approximately 1000 ml aliquots of tap distilled water. Then it was washed with Alkonox TM soap solution, followed by ten more washes with distilled water and finally 5 washes with distilled water (18 mohs conductivity) prepared on a Millipore Milli-Q TM water system.

The flask was charged with 500 ml of "Milli-Q" water. To the water was added 90 mg of reagent grade silver nitrate and the flask was brought to a slow boil with stirring. Immediately after boiling began to occur, 10 ml of 1.0% sodium citrate was added. Within 5 minutes the reaction turned yellow, transitioned through a gray-green color and finally stabilized to a dull translucent green color. Heating near the boiling point was continued for a total of 45 minutes.

Example 15A

SERRS Detection of the Immune Reaction Between Sheep Anti-Theophylline and Bovine Serum Albumin (BSA)—Theophylline Conjugate BSA-theophylline conjugate which contains an average of 17 theophylline molecules per BSA molecule was diluted to 100 µg/ml in 0.02% sodium citrate. Sheep anti-theophylline was diluted to 210 µg/ml in 0.02% sodium citrate. A dye solution was prepared consisting of N,N,dimethylaniline-4 azobenzyo-4-thiocarbamoyl ethyl aminoethyldisulfide at approximately 20 µg/ml in a solvent mixture of ethyl acetate/tetrahydrofuran/methanol/water (1/1/2/2 by volume). Pre-incubated 20 µl of BSA-theophylline with 14 µl of sheep anti-theophylline for 10 minutes at 37° C. Then 0.5 mi of silver colloid was added. No aggregation was visibly evident. Then 5 µl of dye solution was added and incubated for 90 minutes at 37° C. Immediately after incubation the surface-enhanced Raman spectrum was recorded using an argon ion laser at 488 nm excitation. The spectrum displayed a strong peak at a Raman shift of 1410 $cm^{-1}$, attributable to the diazo functionality of the dye

Example 15B

Control Experiment

In this experiment an anti-streptococus IgG was substituted at the same concentration, for the anti-theophylline IgG, and the same assay conditions as described in Example 15A were followed. Recording of the Raman spectrum showed several peaks attributable to the dye, where the strongest peak was at a Raman shift of 1410 $cm^{-1}$ from the laser wavelength of 488 nm The intensities of these peaks were only 13% of those generated when anti-theophylline was used.

Example 15C

Control Experiment

In this experiment BSA was substituted for the BSA-theophylline conjugate used in conjunction with anti-theophylline antibody under the same concentrations and conditions as described in Example 15A were followed. Recording of the Raman spectrum showed several peaks attributable to the dye, where the strongest peak was at a Raman shift of 1410 cm$^{-1}$ from the laser wavelength of 488 nm The intensities of these peaks were only 16% of those generated when BSA-theophylline conjugate was used.

Example 15D

A dye-labeled metal colloid could be prepared by mixing 5 ul of a 20 μg/ml dye solution with 1–0.5 ml of colloid, and this reagent can be used in example 15A, in place of the sequential addition of colloid followed by dye. To prevent destabilization of the colloid by the dye, the colloid can be overcoated with a dilute (less than 1 μg/ml) solution of another protein such as bovine serum albumin or commercial surfactants such as Tween 20 or Brij 35 prior to addition of the dye.

Example 16

No-Wash Immunoassay for Theophylline using a Competitive Format

Theophylline was dissolved at 140, 70, 30, 6, 2.8, 0.55 and 0.0 μg/ml in 0.02% citrate Aliquoted 100 μl samples of each concentration into test tubes. Aliquoted 14 μl of sheep anti-theophylline as described in example 7a into each of the tubes and incubated for 30 minutes at room temperature. Added 20 μl BSA-theophylline conjugate as described in example 7a to each tube, mixed by vortexing and added sequentially 0.5 ml of silver colloid and 5 μl of dye solution as described in example 15A. Within one minute the sample was placed in the Raman spectrometer and the surface-enhanced Raman spectrum was recorded using an argon ion laser at 488 nm excitation. The relative intensity of the peak at a Raman shift of 1410 cm$^{-1}$, attributable to the diazo functionality of the dye, was measured and plotted as a function of theophylline concentration present in the colloid test sample, as shown in FIG. 10.

Example 17

Preparation of a conjugate of Biotinylated Bovine Serum Albumin with 4-dimethylaminoazobenzene-4'-isothiocyanate (Biotin-BSA-DAB). Abbreviation for the conjugate is (Biotin-BSA-DAB)

Biotinylated bovine serum albumin (purchased from Sigma Chemical Co.) (2 mg) was dissolved in 2 ml of 1% NaHCO$_3$, pH 8.6, and a 20 μl aliquot of a solution of 1 mg/ml 4-dimethylaminoazobenzene-4'-isothiocyanate in dimethyl formamide was added. The mixture was stirred overnight, then desalted on a Sephadex G-25 (coarse) column (1×30 cm).

Example 18

No Wash Detection of the Inhibition of Binding of Biotinylated Bovine Serum Albumin (BSA) to Streptavidin-Coated Silver Colloids By SERRS.

Streptavidin (408 μl, at 0.1 mg/ml in 0.02% citrate buffer) was incubated with 24 ml of silver colloid for 1 hour at 37 deg. C. After incubation, 24 aliquots of "avidin-coated" colloid were placed in small glass test tubes. Aliquots of 12 μl of 4.4 mg/ml biotin in citrate buffer were added to twelve of the tubes. All 24 of the tubes were incubated at 37 deg. C. for 45 minutes. Six dilutions of biotinylated BSA-DAB conjugate at 12.5, 25, 50, 75, 100 and 125 μg/ml in citrate were prepared. 100 μl each of the diluted biotinylated BSA-DAB conjugate solutions were added to two duplicate 1 ml samples of both the avidin coated colloid, and the avidin coated colloid which was pre-exposed to free biotin and the SERRS spectra were recorded. The samples which had been pre-exposed to free biotin showed weaker signals than those which did not come in contact with biotin. The duplicates were averaged and the differences between the biotin-pre-exposed and unexposed samples were plotted as a function of the concentration of biotin-BSA-DAB added and the results are shown in FIG. 11.

Example 19

Hepatitis B Surface Antigen (HBsAg) SERRS Assay on a Membrane

Anti-HbsAg can be immobilized in a spot midway along a 0.5×4 cm nitrocellulose strip. A blotter can be fixed to the top end of the strip. The strip is contacted at the bottom to a sample consisting of 120 μl of human plasma containing a defined amount of HBsAg. The sample is drawn up the strip by capillary action past the immobilized antibody, so that HBsAg in the sample would be captured by the immobilized anti-HBsAg antibody. This is followed sequentially by 10 μl of a 2 μl/ml biotinylated anti-HBsAg antibody (an ancillary specific binding member) and a metal colloid containing surface immobilized anti-biotin antibody and a label dye capable of exhibiting a strong SERRS spectrum. Alternatively, the label dye can be attached to the anti-biotin antibody which is immobilized on the metal particle. The colloidal particle-dye-antibody complex will become localized near the spot where the anti-HbsAg is immobilized on the strip. This occurs via a ligand binding reaction between the nitrocellulose immobilized anti-HBsAg binding to the analyte (HbsAg) which binds to the biotinylated anti-HBsAg which binds to the colloid-immobilized anti-biotin antibody. The presence and amount of the analyte (HbSAg) can be determined by measuring the SERRS spectrum of the dye label in the aforementioned spot midway along the strip.

Example 20

Figure 12A:
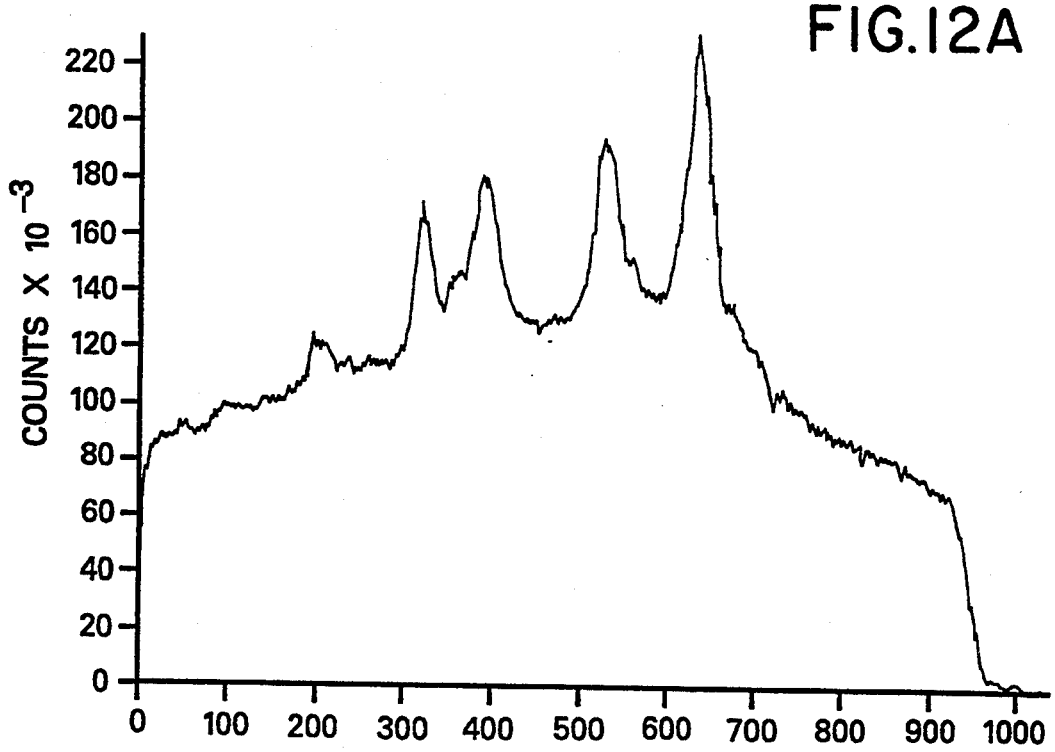
FIGS. 12A and 12B show surface-enhanced Raman scattering (SERRS) spectra of 20:1 mixture of methylene blue:oxazine 725 on silver colloid, where the colloid was made either using (A) hydrogen and (B) citrate as the reducing agent.
Figure 12B:
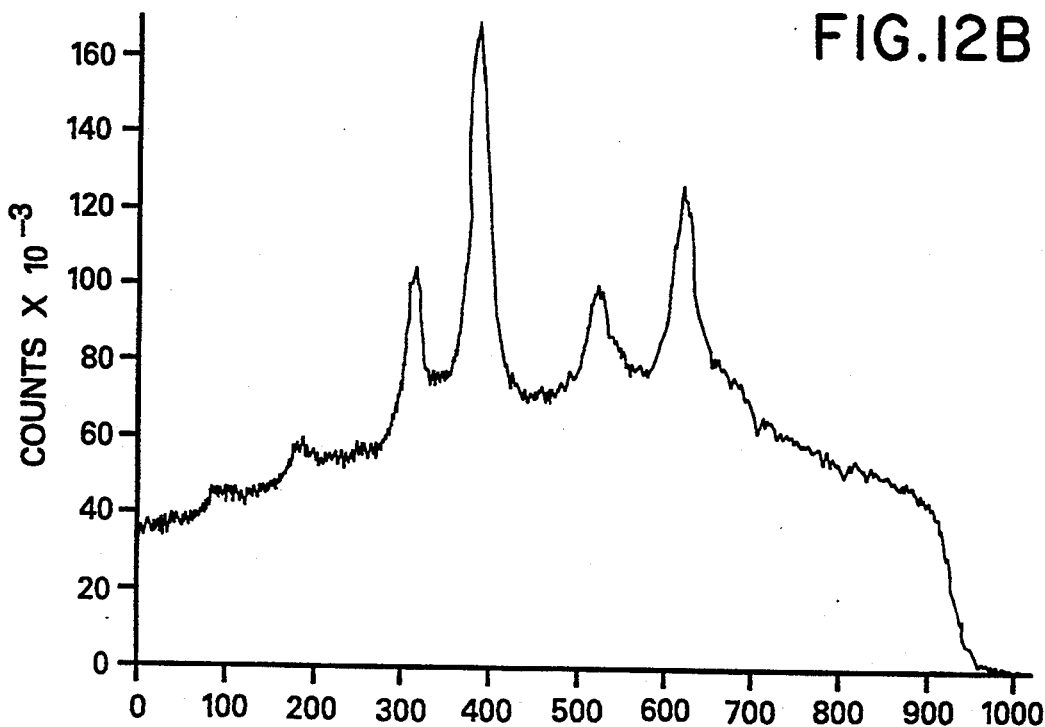

Demonstration of SERRS on Silver Colloids Made by Both Citrate and Hydrogen Reduction of Silver Nitrate A dilute solution mixture at 20 to 1 by weight of methylene blue dye mixed with oxazine 725 dye, respectively, was made in water. Equal volumes were added to separate samples of silver colloid. One sample was made by reduction of silver nitrate with sodium citrate. The other colloid was made by hydrogen reduction of silver nitrate. Both colloids exhibited the same SERRS spectra with respect to Raman shifted peaks; however, the relative peak intensities show some differences between the colloidal preparations, as shown in FIG. 12.

Example 21

SERRS Assay for Human Chorionic Gonadotropin (HCG)

Antibodies specific for the beta subunit of human chorionic gonadotropin (HCG) are immobilized onto the surface of 50 nm colloidal silver particles to produce a capture reagent. The particles are overcoated with a 0.1% solution of dried milk to supress non-specific binding. A label dye (dimethylaminoazobenzene) capable of exhibiting a distinctive SERRS spectrum is attached to a second antibody which is specific for the alpha subunit of HCG to form a conjugate. The capture reagent is diluted in 0.01 molar citrate buffer, pH 7.4 to a concentration of 0.05%, and mixed with a solution containing the conjugate at a concentration of 20 ug/ml in the same citrate buffer. Individual 50 ul aliquots are taken from each of six test samples containing 0-200 ml.U. of HCG and each is mixed with a 100 ul aliquot of the capture reagent-conjugate mixture. The mixtures are then allowed to incubate at room temperature for 30 min. During this time the beta subunit of any HCG present becomes bound to the particles through the immobilized anti-beta antibody, while the alpha subunit becomes bound to the conjugate through the anti-alpha antibody, thereby binding the Raman label to the particles, the total amount bound depending on the quantity of HCG present. After incubation, each mixture is applied to a separate filter assembly consisting of a filter supported by an absorbant pad, and the liquid containing the unbound conjugate is allowed to be drawn through the filter into the absorbant pad beneath. The surfaces of the filter retains the particles and any conjugate bound to them through the HCG analyte. The surface of the filters are then illuminated with light sufficient to cause the captured label molecules to display a SERS or SERRS spectrum, the close packing of the particles on the filter surface serving to further amplify the enhancement effect.

The foregoing description of the presently preferred embodiments of the present invention has been offered for purposes of illustration and description. It is not intended to limit the scope of the invention, which is defined by the appended claims and their equivalents. Various modifications and variations of the preferred embodiments are possible in light of the above teachings and will be apparent to persons skilled in the art. Such modifications and variations do not depart from the spirit or scope of the invention and it is therefore intended that the scope of the invention be defined by the appended claims, including all equivalents.

What is claimed is:

1. A method for determining the presence or amount of an analyte, if any, in a test sample by monitoring an analyte-mediated ligand binding event in a test mixture the method comprising:

forming a test mixture comprising the test sample and a particulate capture reagent, said particulate capture reagent comprising a specific binding member attached to a particulate having a surface capable of inducing surface-enhanced Raman light scattering and also having attached thereto a Raman-active label wherein said specific binding member attached to the particulate is specific for the analyte, an analyte-analog or an ancillary binding member;

providing a chromatographic material having a proximal end and a distal end, wherein the distal end of said chromatographic material comprises a capture reagent immobilized in a capture situs and capable of binding to the analyte;

applying the test mixture onto the proximal end of said chromatographic material;

allowing the test mixture to travel from the proximal end toward the distal end by capillary action;

illuminating the capture situs with a radiation sufficient to cause a detectable Raman spectrum; and monitoring differences in spectral characteristics of the detected surface-enhanced Raman scattering spectra, the differences being dependent upon the amount of analyte present in the test mixture.

2. The method according to claim 1 wherein the radiation causes a surface-enhanced resonance Raman scattering.

3. The method according to claim 1 further comprising adding an enhancer, selected from the group consisting of salt, buffer preparation, sugar and polymer, to the test mixture.

4. A method for determining the presence or amount of an analyte, if any, in a test sample by monitoring an analyte-mediated ligand binding event in a test mixture, the method comprising:

forming a test mixture comprising the test sample, an analyte-analog, and a particulate capture reagent comprising a specific binding member attached to a particulate having a surface capable of inducing surface-enhanced Raman light scattering and also attached thereto a Raman-active label wherein said specific binding member attached to the particulate is specific for the analyte, an analyte-analog or an ancillary binding member;

providing a chromatographic material having a proximal end and a distal end, wherein the distal end of said chromatographic material contains a capture reagent immobilized in a capture situs and capable of binding to the analyte of the analyte-analog;

applying the test mixture onto the proximal end of said chromatographic material;

allowing the test mixture to travel from the proximal end toward the distal end by capillary action;

illuminating the capture situs with a radiation sufficient to cause a detectable Raman spectrum; and monitoring differences in spectral characteristics of the surface-enhanced Raman scattering spectra, the differences being dependent upon the amount of the analyte present in the test mixture.

5. The method according to claim 4 wherein the radiation causes a surface-enhanced resonance Raman scattering.

6. The method according to claim 4 further comprising adding an enhancer, selected from the group consisting of salt, buffer preparation, sugar and polymer, to the test mixture.

* * * * *